US012636292B2

(12) United States Patent
Wu et al.

(10) Patent No.: US 12,636,292 B2
(45) Date of Patent: May 26, 2026

(54) METHOD AND COMPOSITION FOR REVERSING AND/OR INHIBITING ATHEROSCLEROSIS

(71) Applicant: ARJIL BIOTECH HOLDING COMPANY LIMITED, Hsinchu (TW)

(72) Inventors: Yeh B Wu, Hsinchu City (TW); Jir-Mehng Lo, Hsinchu City (TW); Hui Ju Liang, Taipei City (TW); Pei-Hsin Lin, Hsinchu County (TW); Chieh-Hsi Wu, Taichung City (TW); Chung-Hsin Wu, Taipei (TW)

(73) Assignee: ARJIL BIOTECH HOLDING COMPANY LIMITED, Hsinchu (TW)

( * ) Notice: Subject to any disclaimer, the term of this patent is extended or adjusted under 35 U.S.C. 154(b) by 239 days.

(21) Appl. No.: 18/409,486

(22) Filed: Jan. 10, 2024

(65) Prior Publication Data

US 2024/0148753 A1 May 9, 2024

Related U.S. Application Data

(63) Continuation-in-part of application No. 16/851,637, filed on Apr. 17, 2020, now abandoned.

(60) Provisional application No. 62/835,663, filed on Apr. 18, 2019.

(51) Int. Cl.
*A61P 9/10* (2006.01)
*A61K 31/575* (2006.01)

(52) U.S. Cl.
CPC .............. *A61K 31/575* (2013.01); *A61P 9/10* (2018.01)

(58) Field of Classification Search
CPC ........................................................ A61P 9/10
See application file for complete search history.

(56) References Cited

U.S. PATENT DOCUMENTS

| | | | |
|---|---|---|---|
| 8,658,629 | B2 | 2/2014 | Lin |
| 2006/0251673 | A1 | 11/2006 | Hwang et al. |
| 2015/0050315 | A1 | 2/2015 | Pan et al. |
| 2017/0035829 | A1 | 2/2017 | Jia et al. |
| 2018/0353520 | A1 | 12/2018 | Wu et al. |
| 2020/0330485 | A1 | 10/2020 | Wu et al. |

FOREIGN PATENT DOCUMENTS

| | | | | | |
|---|---|---|---|---|---|
| CN | 104367600 | A | * | 2/2015 | ............ A61K 36/07 |
| CN | 104606260 | B | * | 1/2018 | |
| WO | WO 2009/052711 | A1 | | 4/2009 | |

OTHER PUBLICATIONS

International Search Report and Written Opinion of the International Searching Authority for International Application No. PCT/US20/28693, dated Jul. 21, 2020, with an English translation.

Wu et al., "Effects of Antrodia Camphorata, Salvia Miltiorrhiza and Antrodia Camphorata-Fermented Salvia Miltiorrhiza on Antithrombosis and Anticoagulation in Rats," International Journal of Biological & Pharmaceutical Research, 2015, vol. 6, No. 5, pp. 375-381, 7 pages total.

* cited by examiner

*Primary Examiner* — Qiuwen Mi
(74) *Attorney, Agent, or Firm* — Birch, Stewart, Kolasch & Birch, LLP

(57) ABSTRACT

The present invention pertains to a method for alleviating atherosclerosis in a subject comprising administrating to said subject a composition or pharmaceutical composition comprising Antcin K.

6 Claims, 12 Drawing Sheets

METHOD AND COMPOSITION FOR REVERSING AND/OR INHIBITING ATHEROSCLEROSIS

CROSS REFERENCE TO RELATED APPLICATIONS

This application is a continuation-in-part of U.S. patent application Ser. No. 16/851,637, claiming the benefit of and priority to U.S. Provisional Application Ser. No. 62/835,663, filed Apr. 18, 2019, which is incorporated herein by reference in their entirety.

FIELD OF THE INVENTION

The present invention provides a method and composition of reversing and/or inhibiting atherosclerosis.

BACKGROUND OF THE INVENTION

Atherosclerosis is a fundamental pathological process that is known to cause some serious cardiovascular diseases, including stroke and coronary artery disease. Although classical risk factors for atherosclerosis may include dyslipoproteinaemia, diabetes, cigarette smoking, hypertension and genetic abnormalities, hypercholesterolaemia is considered one of the main triggers of atherosclerosis. The increase in plasma cholesterol levels results in changes of the arterial endothelial permeability that allow the migration of lipids, especially low-density lipoprotein cholesterol (LDL-C) particles, into the arterial wall to form a plaque. When a plaque covers more than 40% of internal elastic layer of the vessel, the arterial channel is considered to be occupied, thereby obstructing the blood flow.

Currently, treatment for atherosclerosis include medications to lower cholesterol or to decrease clotting, and surgical management. Surgical therapies only treat isolated lesions, and plaques downstream from the treated lesion may continue to obstruct blood flow. Furthermore, surgical therapies are associated with the late complication of restenosis. On the other hand, medications to lower cholesterol such as statins reduce cardiovascular events by only about 20%-40%.

What is needed for atherosclerosis treatment not only slows progression of lesions, but also causes regression and shrinkage of established plaques.

BRIEF SUMMARY OF THE INVENTION

It is unexpectedly found in the present invention that a preparation of *Antrodia camphorata* and active ingredients of *Antrodia camphorata* are effective to reverse and/or inhibit atherosclerosis.

It was ascertained in the examples that the preparation of *Antrodia camphorata* was able to reverse and inhibit an aortic fatty streak lesion, a plaque formation and a vascular restenosis.

It is an object of the present invention to provide a method for preventing and/or treating atherosclerotic disease, comprising administering to a subject in need thereof a preparation of *Antrodia camphorate* and/or active ingredients of *Antrodia camphorata.*

Actually, it would be derived from the findings that the reversion or inhibition of atherosclerosis by inhibiting the aortic fatty streak lesion, the plaque formation, and the vascular restenosis to inhibit ischemic stroke, cardiovascular disease, peripheral arterial disease and major organ vascular atherosclerosis.

In another object, the present invention provides a pharmaceutical composition for preventing and/or treating atherosclerotic disease, which comprises a therapeutically effective amount of a preparation of *Antrodia camphorate* and/or active ingredients of *Antrodia camphorata*, and a pharmaceutically acceptable carrier.

In one embodiment of the invention, the preparation of *Antrodia camphorate* includes but not is limited to an extract of *Antrodia camphorate*, an extract of a dish culture of *Antrodia camphorate*, an extract of *Antrodia camphorata* fruit body, and active compounds isolated from the above-mentioned extracts.

In one example of the invention, the active compound may be one or more selected from the group consisting of:

(Ia)

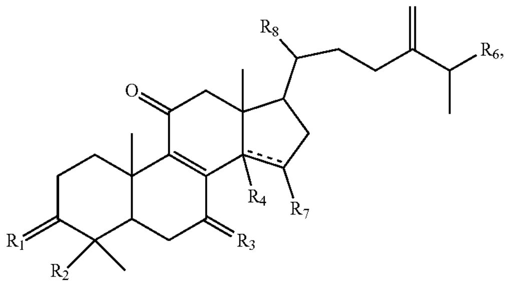

, (Ib)

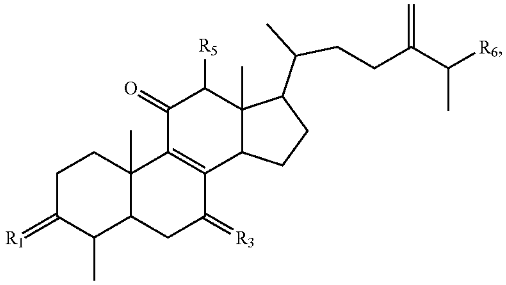

, (Ic)

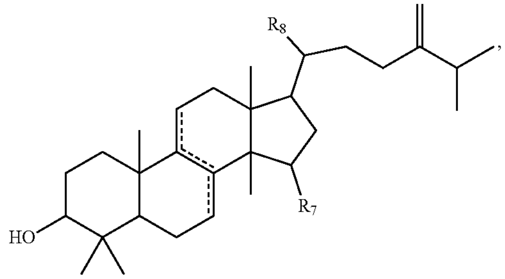

, (Id)

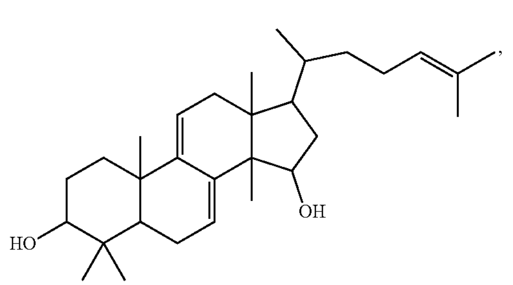

, and

-continued (Ie)

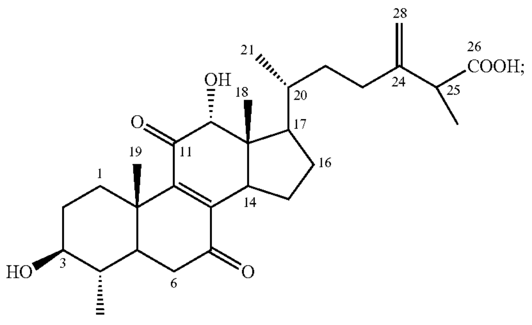

wherein $R_1$ is O, α-OH or β-H; $R_2$ is H or OH; $R_3$ is O, α-H, β-OAc or $H_2R_4$ is H or OH; $R_5$ is H or OH; $R_6$ is COOH or $COO(CH_2)n-CH_3R_7$ is H, OH, or OAc; $R_8$ is $CH_3$ or COOH; the dotted line represents a single bond or a double bond; n is an integer from 0-3.

In one particular example of the present invention, the compound is dehydroeburicoic acid:

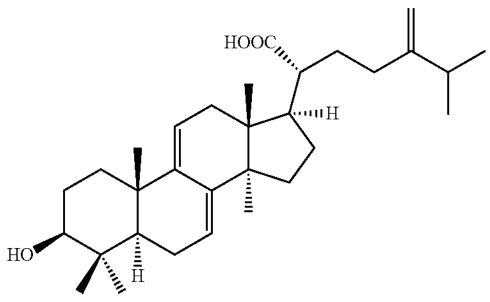

In another example of the present invention, the compound is dehydrosulphurenic acid (dehydrosulfurenic acid):

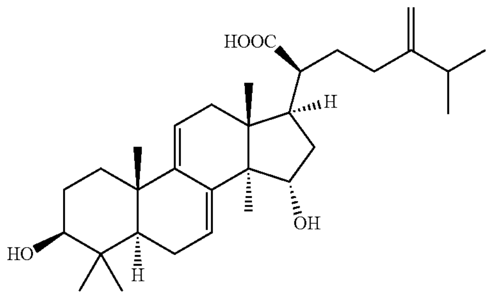 [SMILES: C=C(CC[C@H](C(=O)O)[C@H]1C[C@H](O)[C@@]2(C)C3=CC[C@H]4C(C)(C)[C@@H](O)CC[C@]4(C)C3=CC[C@]12C)C(C)C]

In one example of the present invention, the compound is antcin A:

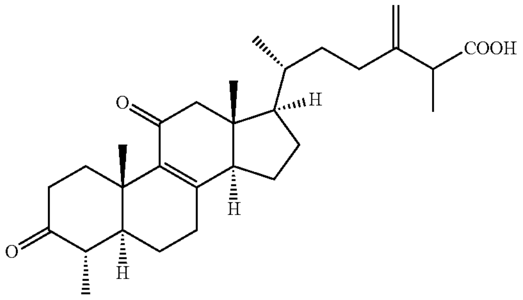 [SMILES: C=C(CC[C@@H](C)[C@H]1CC[C@H]2C3=C(C(=O)C[C@]12C)[C@@]1(C)CCC(=O)[C@@H](C)[C@@H]1CC3)C(C)C(=O)O]

In one example of the present invention, the compound is antcin B:

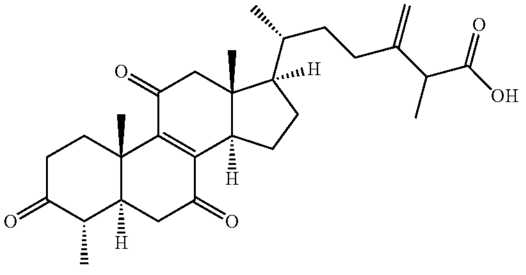 [SMILES: C=C(CC[C@@H](C)[C@H]1CC[C@H]2C3=C(C(=O)C[C@]12C)[C@@]1(C)CCC(=O)[C@@H](C)[C@@H]1CC3=O)C(C)C(=O)O]

In one example of the present invention, the compound is antcin C:

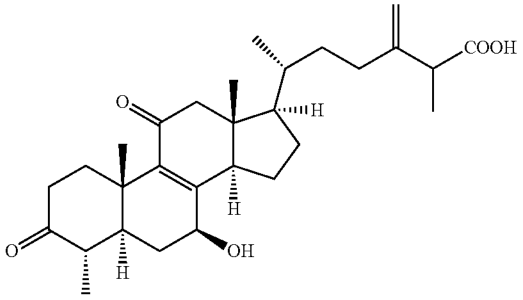 [SMILES: C=C(CC[C@@H](C)[C@H]1CC[C@H]2C3=C(C(=O)C[C@]12C)[C@@]1(C)CCC(=O)[C@@H](C)[C@@H]1C[C@@H]3O)C(C)C(=O)O]

In one example of the present invention, the compound is antcin H:

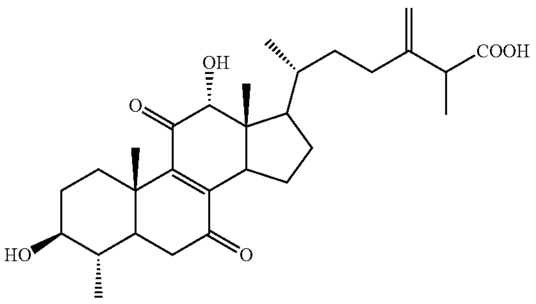 [SMILES: C=C(CC[C@@H](C)C1CCC2C3=C(C(=O)[C@H](O)[C@@]21C)[C@@]1(C)CC[C@H](O)[C@@H](C)C1CC3=O)C(C)C(=O)O]

In one example of the present invention, the compound is antcin K:

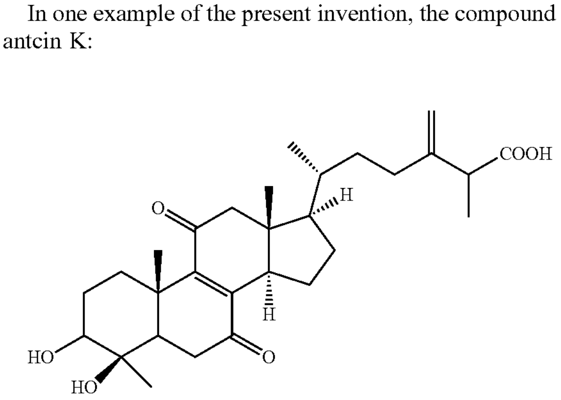

In one further aspect, the present invention provides a method for preventing or treating an atherosclerotic disease comprising administering to a subject in need thereof a therapeutically effective amount of a composition/pharmaceutical composition as disclosed herein, and at least one additional atherosclerosis therapeutic agent.

In one further yet aspect, the present invention provides a method A method for alleviating atherosclerosis in a subject, which comprises administering to a subject in need thereof an effective amount of a composition or pharmaceutical composition containing a compound of the structure below:

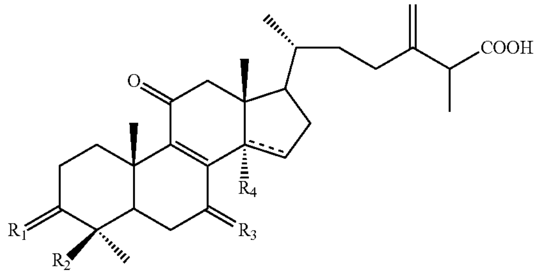

wherein $R_1$ is O or OH, $R_2$ is H or OH, $R_3$ is Hz, O, OH; and $R_4$ is H, or HO.

In one example of the invention, the compound is antcin K having the structure below:

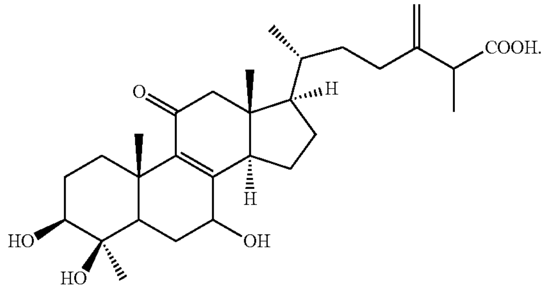 [SMILES: C=C(CC[C@@H](C)[C@H]1CC[C@H]2C3=C(C(=O)C[C@]12C)[C@@]1(C)CC[C@H](O)[C@](C)(O)C1CC3O)C(C)C(=O)O]

In the examples of the invention, it was ascertained that the compound can decrease the expression of VCAM-1 that alleviates circulating monocytes adhering to endothelial cells and migrating into subendothelial space; reduce ROS generation and oxidative stress that alleviate the oxidative modification of lipoproteins and phospholipids; enhance the expression of KLF4 in macrophages and endothelial cells that decrease lipid deposition and prevent macrophages converting into foam cells; decrease the content of TNF-α and IL-1β; and decrease the expression of CD36 that slows transformation of macrophages and endothelial cells to foam cells.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings:

FIG. 10(A) shows the results of the DPPH assay using various concentrations of antcin K treatment for 30 min. L-ascorbic acid is a standard antioxidative compound. FIG. 10(B) shows the comparison of the quantified DPPH free radical scavenging activity among antcin K treatments at 0-50 μg/mL. IC50 of antcin K was 5.76±0.14 μg/mL (n=3 for each group; values are presented as mean±SEM, **p<0.001, one-way ANOVA followed by the Student-Newman-Keuls multiple comparison post hoc test).

FIG. 11(A) provides the MTT assay showed the cell viability of vascular endothelial cells under different concentrations of palm acid oil (PA) treatments for 24 h. FIG. 11(B) provides the comparison of the quantified cell viability among vascular endothelial cells with palm acid oil treatments at 0, 0.25, 0.50, 0.75, 1.00, and 2.00 mM. In this experiment, IC50 cell viability of endothelial cells for palm acid oil treatment was 2.0 mM. The 75% survival rate of vascular endothelial cells was induced by palm acid oil treatment at 0.75 mM (indicated by the arrow) that was selected to induce high-fat damage of vascular endothelial cells and RAW264.7 macrophage cells as our experimental cell models.

FIG. 12(A) MTT assay showed the cell viability of vascular endothelial cells under different concentrations (0, 10, 20, and 50 μg/mL) of antcin K treatments. FIG. 12(B) Comparison of the quantified cell viability among vascular endothelial cells with and without 0.75 mM palm acid oil (PA) treatment and with antcin K treatments at 0, 10, 20, and 50 μg/mL. In this experiment, IC50 cell viability of vascular endothelial cells for antcin K treatment was much larger than 50 μg/mL. (n=3 for each group; values are presented as mean±SEM, **p<0.01, two-way ANOVA followed by the Student-Newman-Keuls multiple comparison post hoc test).

FIG. 14(A) shows the immunofluorescence staining to examine expressions of VCAM-1 (green) and nuclei (blue, DAPI) in vascular endothelial cells and DAPI with and without palm acid oil (PA) treatments, and with and without antcin K treatments. FIG. 14(B) shows the comparison of the quantified expression of VCAM-1 of vascular endothelial cells with and without 0.75 mM palm acid oil treatment, and with and without 20 μg/mL antcin K treatment (n=3 for each group; values are presented as mean±SEM, **p<0.01, one-way ANOVA followed by the Student-Newman-Keuls multiple comparison post hoc test).

FIG. 15(A) provides the results of the cell migration assay for antcin K, which affected the migration ability of RAW264.7 macrophages toward vascular endothelial cells with palm oil-induced high-fat damage. FIG. 15(B) shows that antcin K treatments enhanced the migration ability of RAW264.7 macrophages (indicated by the arrow) toward vascular endothelial cells with palm oil-induced high-fat damage. FIG. 15(C) shows the comparison of the quantified expressions of the TNF-α and IL-1β among RAW264.7 macrophages with and without 0.75 mM palm acid oil (PA) treatment, and with antcin K treatments at 0 and 20 μg/mL (n=3 for each group; values are presented as mean±SEM, **p<0.01, * p<0.05, two-way ANOVA followed by the Student-Newman-Keuls multiple comparison post hoc test).

FIG. 17(A) shows the immunofluorescence staining to examine expressions of CD36 (green) and nuclei (blue, DAPI) in vascular endothelial cells with and without palm acid oil (PA) treatments, and with and without antcin K treatments. FIG. 17(B) shows the comparison of the quantified expression of CD36 of vascular endothelial cells with and without 0.75 mM palm acid oil (PA) treatment, and with and without 20 μg/mL antcin K treatment (n=3 for each group; values are presented as mean±SEM, * $p<0.05$, ** $p<0.01$, one-way ANOVA followed by the Student-Newman-Keuls multiple comparison post hoc test).

FIG. 18(A) shows the immunofluorescence staining to examine expressions of KLF4 (green) and nuclei (blue, DAPI) in vascular endothelial cells with and without palm acid oil (PA) treatment, and with and without antcin K treatments. FIG. 18(B) shows the comparison of the quantified expression of KLF4 of vascular endothelial cells with and without 0.75 mM palm acid oil treatment, and with and without 20 μg/mL antcin K treatment (n=3 for each group; values are presented as mean±SEM, ** $p<0.01$, one-way ANOVA followed by the Student-Newman-Keuls multiple comparison post hoc test).

DETAILED DESCRIPTION OF THE INVENTION

Figure 1:
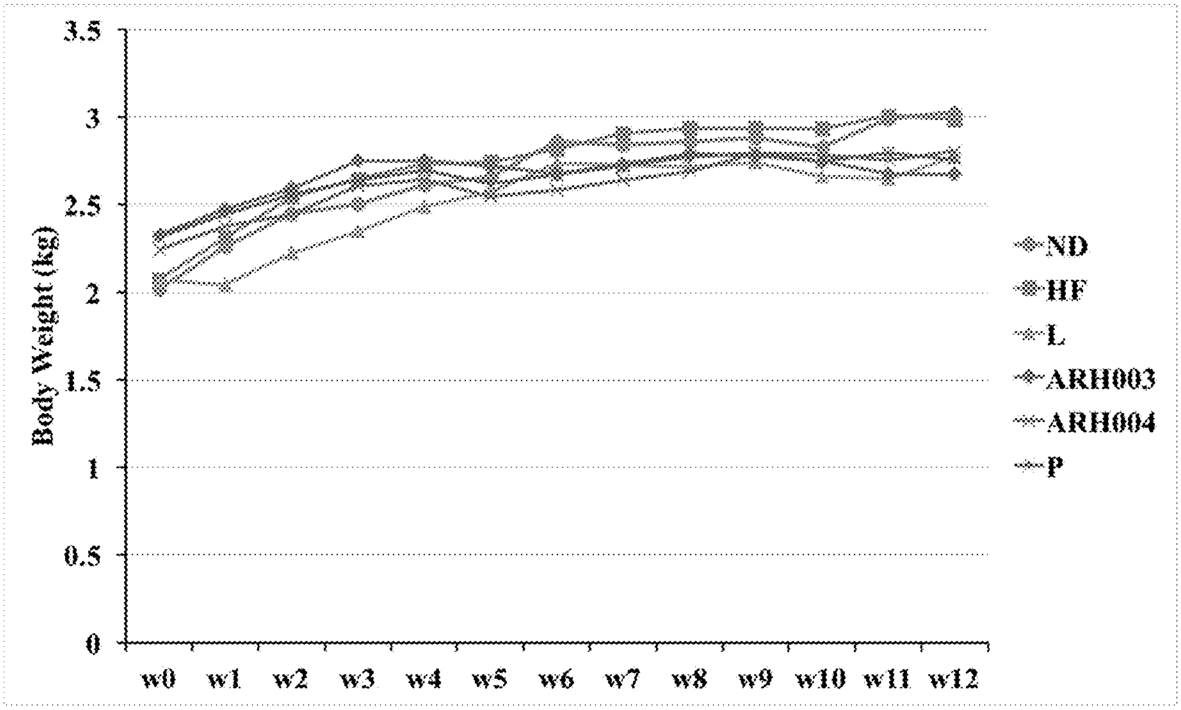
FIG. 1 shows changes of body weight. ND, standard rabbit chow; HF, standard rabbit chow containing 0.5% cholesterol; L, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; P, standard rabbit chow containing both 0.5% cholesterol and 10 mg/kg Pure compound.

The above summary of the present invention will be further described with reference to the embodiments of the following examples. However, it should not be understood that the content of the present invention is only limited to the following embodiments, and all the inventions based on the above-mentioned contents of the present invention belong to the scope of the present invention.

Unless defined otherwise, all technical and scientific terms used herein have the same meaning as commonly understood by a person skilled in the art to which this invention belongs.

As used herein, the singular forms "a", "an" and "the" include plural referents unless the context clearly dictates otherwise. Thus, for example, reference to "a sample" includes a plurality of such samples and equivalents thereof known to those skilled in the art.

The present invention provides a method for preventing and/or treating atherosclerotic disease, comprising administering to a subject in need thereof a preparation of *Antrodia camphorate* and/or active ingredients of *Antrodia camphorata.*

The present invention also provides a composition/pharmaceutical composition for preventing and/or treating atherosclerotic disease, which comprises a therapeutically effective amount of a preparation of *Antrodia camphorate* and/or active ingredients of *Antrodia camphorata*, and a pharmaceutically acceptable carrier.

According to the invention, the preparation of *Antrodia camphorate* includes but not is limited to an extract of *Antrodia camphorate*, an extract of a dish culture of *Antrodia camphorate*, an extract of *Antrodia camphorata* fruit body, and active compounds isolated from the above-mentioned extracts, and the derivatives thereof.

More particularly, the active compounds isolated from *Antrodia camphorata* are one or more selected from the group consisting of the following:

(1)

(Ia)

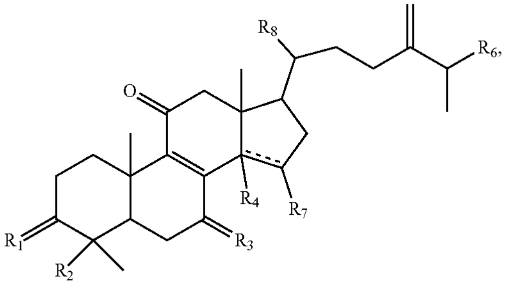

(Ib)

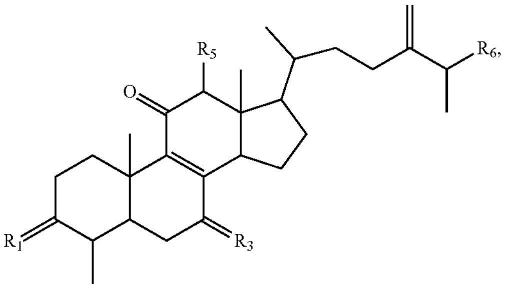

(Ic)

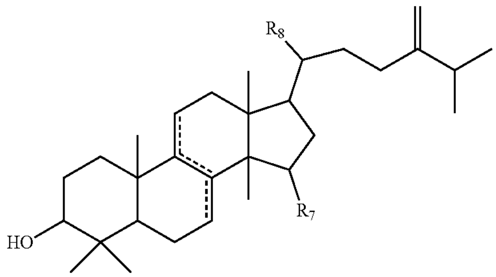

, (Id)

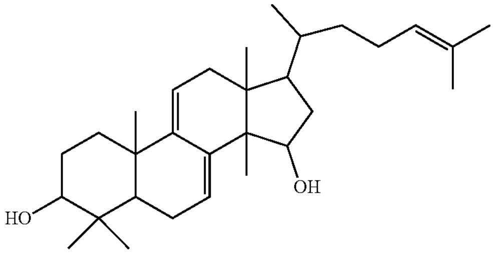

, or

-continued (Ie)

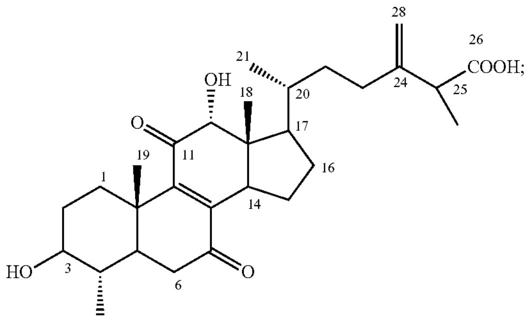

wherein $R_1$ is O, α-OH or β-H; $R_2$ is H or OH; $R_3$ is O, α-H, β-OAc or Hz; $R_4$ is H or OH; $R_5$ is H or OH; $R_6$ is COOH or $COO(CH_2)n-CH_3R_7$ is H, OH, or OAc; $R_8$ is $CH_3$ or COOH; the dotted line represents a single bond or a double bond; n is an integer from 0-3.

In the example of the invention, the compound may be:

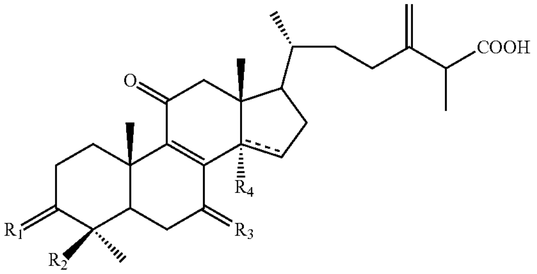

| | $R_1$ | $R_2$ | $R_3$ | $R_4$ | Δ |
|---|---|---|---|---|---|
| Antcin A | O | H | $H_2$ | H | |
| Antcin B | O | H | O | H | |
| Antcin C | O | H | β-OH | H | |
| Antcin D | O | H | O | OH | |
| Antcin E | O | H | $H_2$ | | 14 |
| Antcin F | O | H | β-OH | | 14 |
| Antcin K | α-OH | OH | β-OH | H | |

In another example of the invention, the compound may be:

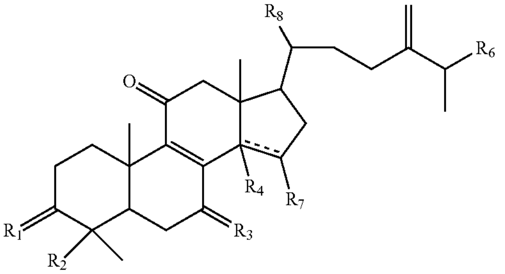

$R_7$ = H; $R_8$ = $CH_3$

| | $R_1$ | $R_4$ | $R_5$ | $R_6$ |
|---|---|---|---|---|
| Zhankuic acid B | β-H<br>α-OH | H | H | COOH |
| Zhankuic acid C | β-H<br>α-OH | H | OH | COOH |

-continued

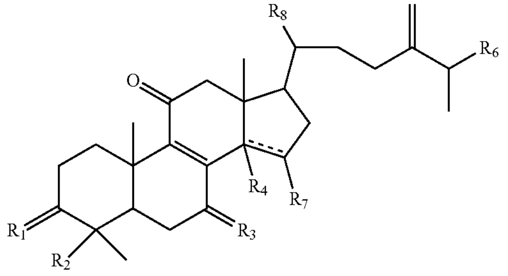

$R_7$ = H; $R_8$ = $CH_3$

| | $R_1$ | $R_4$ | $R_5$ | $R_6$ |
|---|---|---|---|---|
| Zhankuic acid D | O | H | H | COOEt |
| Zhankuic acid E | β-H<br>α-OH | H | OH | COOEt |

In one yet example of the invention, the compound may be:

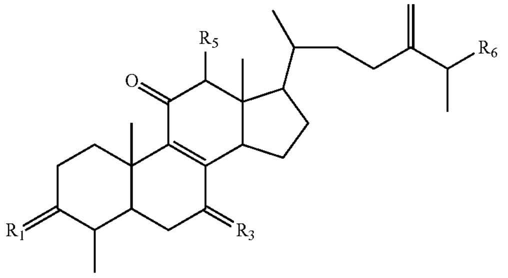

| | $R_1$ | $R_3$ | $R_5$ |
|---|---|---|---|
| methyl antcinate B | O | O | H |
| methyl antcinate G | O | β-OAc<br>α-H | H |
| methyl antcinate H | β-H<br>α-OH | O | OH |
| | O | $H_2$ | H |

In further example of the invention, the compound may be:

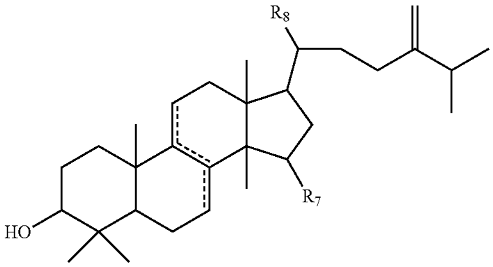

| | $R_7$ | $R_8$ | Δ |
|---|---|---|---|
| dehydroeburicoic acid | H | COOH | 7,9 (11) |
| eburicol | H | $CH_3$ | 8 |
| 15a-acetyl-dehydrosulphurenic acid | OAc | COOH | 7,9 (11) |
| dehydrosulphurenic acid | OH | COOH | 7,9 (11) |
| eburicoic acid | H | COOH | 8 |
| Versisponic acid | OAc | COOH | 8 |
| sulphurenic acid | OH | COOH | 8 |

In one particular example of the invention, the compound may be lanostane:

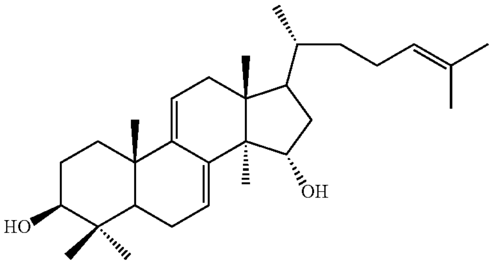

Accordingly, the compound is selected from the group consisting of:

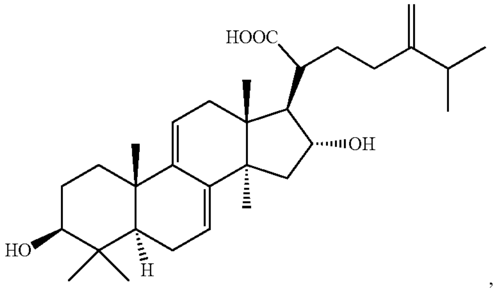

, (dehydrotumolosaeure)

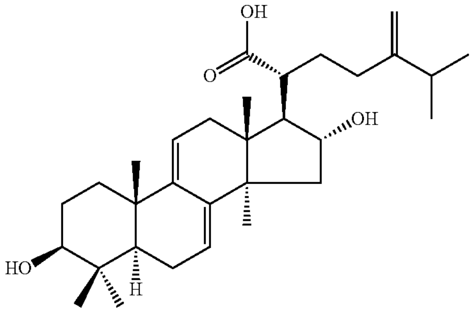

, (dehydrotumulosic acid)

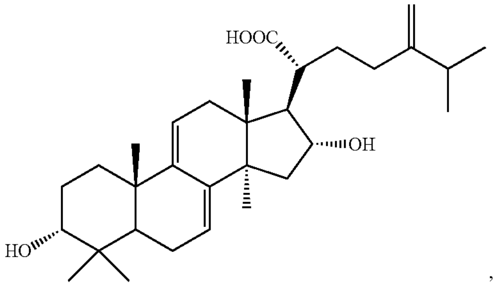

, (3-epi-dehydrotumulosic acid)

-continued

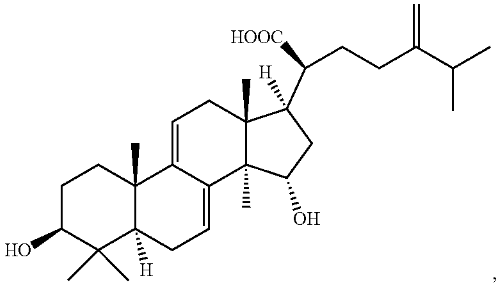

, (dehydrosulphurenic acid)

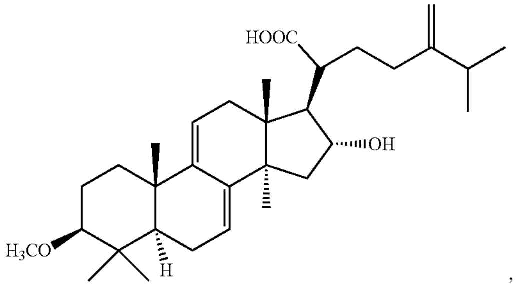

, (dehydrotumolosaeure-methylester)

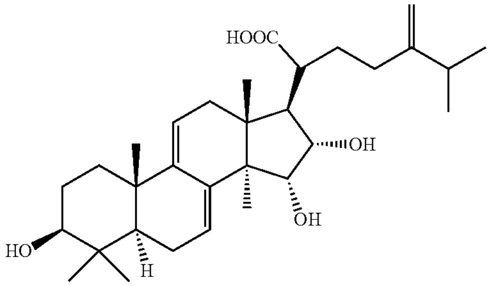

, ((20ξ)-3β,15α,16α-trihydroxy-24-methyllanosta-7,9(11),24(241)-trien-21-oic acid; 15α-hydroxydehydrotumulosic acid)

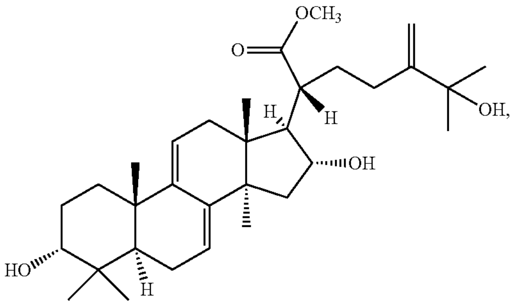

, (methyl 25-hydroxy-3-epidehydrotumulosate(methyl))

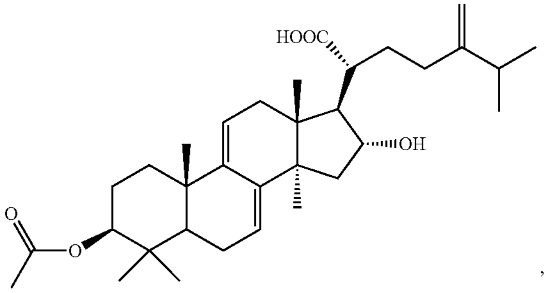

, (dehydropachymic acid)

-continued
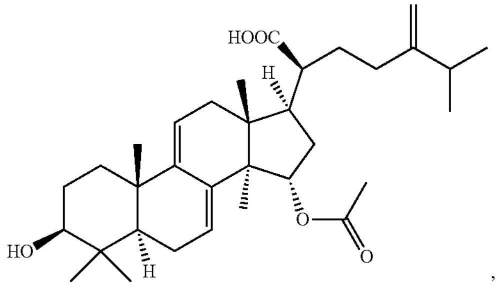
,
(15α-acetyldehydrosulfurenic acid)
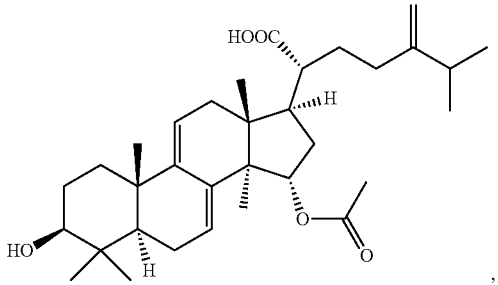
,
(15α-acetyldehydrosulphurenic acid)
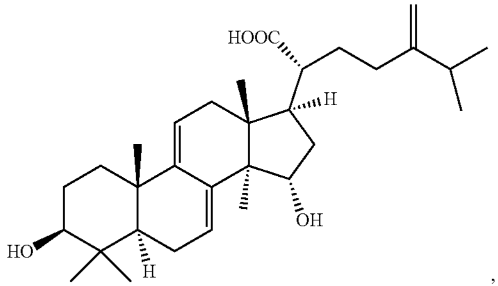
,
(dehydrosulphurenic acid)
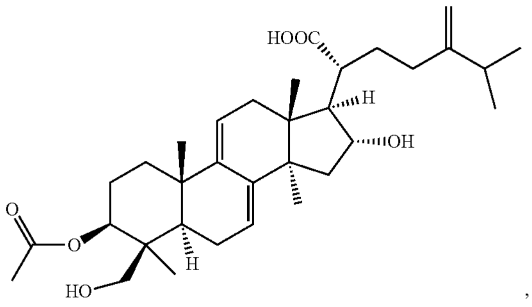
, and
(29-hydroxydehydropachymic acid; (3β,16α)-3-(acetyloxy)-16,29-dihydroxy-24-methylidenelanosta-7,9(11)-dien-21-oic acid)
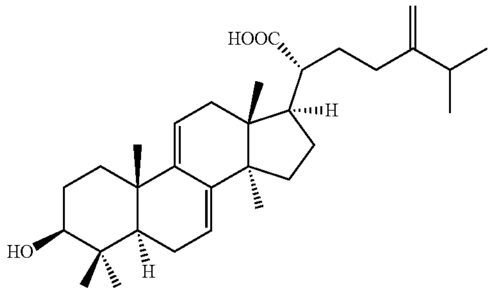
.
(dehydroeburicoic acid)
According to the invention, the compound is selected from the group consisting of
(antcin A)
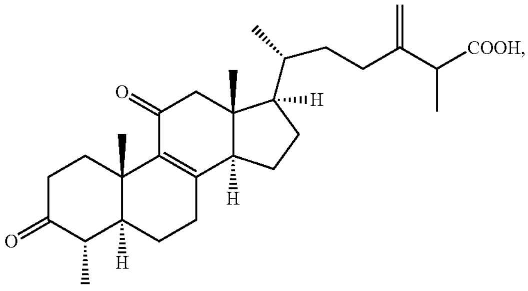
(antcin B)
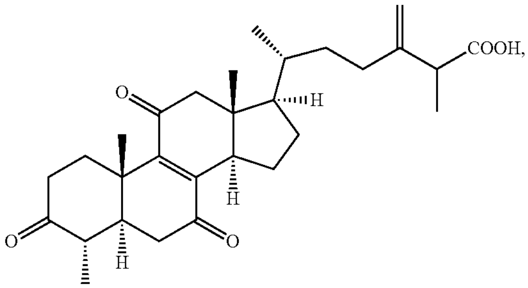
(antcin C)
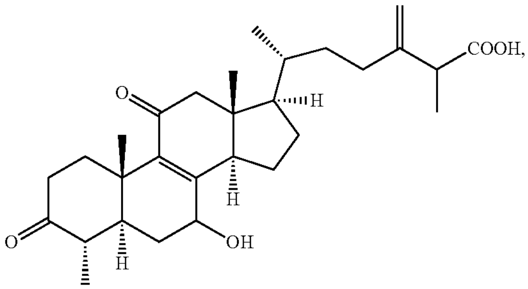
(antcin H)
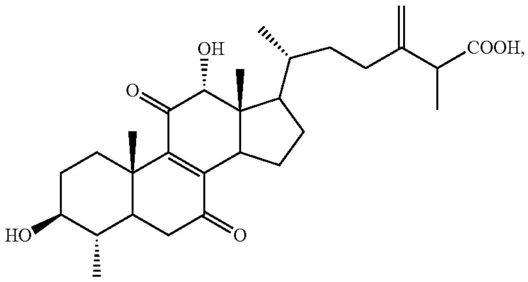
and -continued (antcin K)

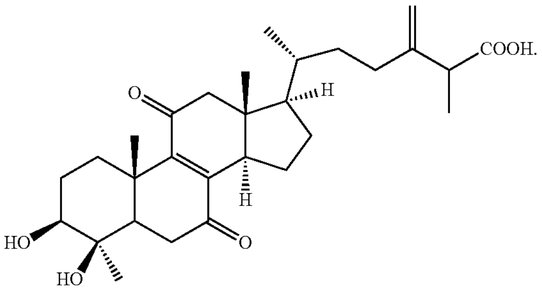

The term "atherosclerotic disease" as used herein refers to atherosclerosis, arteriosclerosis, atheromatous vascular disease, arterial occlusive disease, ischemic stroke, cardiovascular disease, peripheral arterial disease or major organ vascular atherosclerosis, and is characterized by plaque accumulation on vessel walls and vascular inflammation. The plaque is a hallmark of atherosclerotic disease and consists of accumulated intracellular and extracellular lipids, smooth muscle cells, connective tissue, inflammatory cells, and glycosaminoglycans.

The term "preventing," "prevention" or "prevent" or any other forms of "prevent" used herein refers to an action to block a mechanism or a pathway to a particular event or characteristic or a disease. To stabilize or delay the development or progression of a particular event or characteristic or a disease, or to minimize the chances that a particular event or characteristic will occur.

The term "treating," "treatment" or "treat" or any other forms of "treat" as used herein refers to any and all uses which remedy a disease state or symptoms, or otherwise prevent, hinder, retard, or reverse the progression of disease or other undesirable symptoms in any way whatsoever.

The term "inhibiting," "inhibition" or "inhibit" or any other forms of "inhibit" used herein refers to an action of reduction or stop features of an event or characteristic (e.g. atherosclerosis) or a disease.

The term "reducing," "reduction" or "reduce" or any other forms of "reduce" used herein refers to an action of lowering or an event or characteristic (e.g. atherosclerosis). It is understood that this is typically in relation to some standard expected value, in other word it is relative, but that is not always necessary for the standard or relative value to be referred to.

The term "reversing," "reversal" or "reverse" or any other forms of "reverse" used herein refers to an action to recover a patient suffering from a disease to her/his initial healthy state.

The term "subject" as used herein includes human or non-human animals, such as companion animals (e.g. dogs, cats, etc.), farm animals (e.g. cattle, sheep, pigs, horses, etc.), or experimental animals (e.g. rats, mice, guinea pigs, etc.).

The term "therapeutically effective amount" as used herein refers to an amount of a pharmaceutical agent which, as compared to a corresponding subject who has not received such amount, results in an effect in treatment, healing, prevention, or amelioration of a disease, disorder, or side effect, or a decrease in the rate of advancement of a disease or disorder. The term also includes within its scope amounts effective to enhance normal physiological function.

For use in therapy, the therapeutically effective amount of the compound is formulated as a pharmaceutical composition for administration. Accordingly, the invention further provides a pharmaceutical composition comprising a therapeutically effective amount of the preparation of *Antrodia camphorata* or the active compounds isolated from *Antrodia camphorata* and one or more pharmaceutically acceptable carriers.

For the purpose of delivery and absorption, a therapeutically effective amount of the active ingredient according to the present invention may be formulated into a pharmaceutical composition in a suitable form with a pharmaceutically acceptable carrier. Based on the routes of administration, the pharmaceutical composition of the present invention comprises preferably from 0.1% to 100% in weight of the total weight of the active ingredient.

The term "pharmaceutically acceptable carrier" used herein refers to a carrier(s), diluent(s) or excipient(s) that is acceptable, in the sense of being compatible with the other ingredients of the formulation and not deleterious to the subject to be administered with the pharmaceutical composition. Any carrier, diluent or excipient commonly known or used in the field may be used in the invention, depending to the requirements of the pharmaceutical formulation. According to the invention, the pharmaceutical composition may be adapted for administration by any appropriate route, including but not limited to oral, rectal, nasal, topical, vaginal, or parenteral route. In one particular example of the invention, the pharmaceutical composition is formulated for oral administration. Such formulations may be prepared by any method known in the art of pharmacy.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art.

According to the present invention, the composition/pharmaceutical composition described herein may also be administered to a human or a non-human animal in a dietary supplement for decreasing the concentration of LDL-cholesterol and increasing the concentration of HDL-cholesterol in the blood to reduce the risk of atherosclerosis and vascular disease. Dietary supplements incorporating the composition/pharmaceutical composition can be prepared by adding daidzein to a food in the process of preparing the food, independent of the source of the composition/pharmaceutical composition. The foods to which the composition/pharmaceutical composition may be added include almost all foods. For example, the composition/pharmaceutical composition can be added to foods including, but not limited to, meats such as ground meats, emulsified meats, marinated meats, and meats injected with daidzein; beverages such as nutritional beverages, sports beverages, protein fortified beverages, juices, milk, milk alternatives, and weight loss beverages; cheeses such as hard and soft cheeses, cream cheese, and cottage cheese; frozen desserts such as ice cream, ice milk, low fat frozen desserts, and non-diary frozen desserts; yogurts; soups; puddings; bakery products; salad dressings; and dips and spreads such as mayonnaise and chip dips. The composition/pharmaceutical composition is added to the food in an amount selected to deliver a desired dose of the composition/pharmaceutical composition to the consumer of the food.

According to the present invention, the method and composition/pharmaceutical composition described herein could be administrated a subject in combination with at least one additional atherosclerosis therapeutic agent. Exemplified atherosclerosis therapeutic agents which are responsive include, without limitation, statins, fibrates, niacin, Ezetimibe, bile acid sequestrants (such as cholestyramine, colestipol or colesevelam), alirocumab, evolocumab, aspirin, clopidogrel, ticagrelor, prasugrel, and warfarin.

The present invention is further illustrated by the following examples, which are provided for the purpose of demonstration rather than limitation.

EXAMPLES FOR THE EXTRACT

Materials and Methods

1. Preparation of an Extract of *Antrodia camphorata* and its Active Fraction 100 grams of *Antrodia camphorata* fruiting body was heat-recirculated with methanol for 6 hours, and the extract was collected and dried under reduced pressure to obtain 15 grams of the *Antrodia camphorate* methanol extract.

15 grams of the *Antrodia camphorata* methanol extract as obtained above was taken, filled with silicon dioxide, and subjected to a gradient elution with the eluant "hexane ethyl acetate/methanol" in a column separation (3×12 cm) to obtain active fractions, including ARH003 and ARH004. Pure compound derived from *Antrodia camphorata* fruiting body extracts was further isolated.

2. Experimental Model 2 to 3 kg male, New Zealand White rabbits were individually caged and housed in temperature and humidity-controlled rooms. Light-dark cycles were 12 h each. After several days of acclimation, the animals were sequentially assigned to six feeding groups: standard rabbit chow (ND), standard rabbit chow containing 0.5% cholesterol (HF), standard rabbit chow containing both 0.5% cholesterol and 10 mg/kg Lovastatin (L), standard rabbit chow containing both 0.5% cholesterol and 1% ARH003 (ARH003), standard rabbit chow containing both 0.5% cholesterol and 1% ARH004 (ARH004), standard rabbit chow containing both 0.5% cholesterol and 10 mg/kg Pure compound (P).

Except standard rabbit chow, others groups were given standard rabbit chow containing 0.5% cholesterol for 4 weeks. The daily feeding amount for each rabbit was 50 g/kg body weight per day.

Diets were administered for 8 weeks, after the animals had adjusted to their new environment. At the beginning and end of the 12 weeks study, the rabbits were anesthetized by an intramuscular injection of Zoletil 50 (1 mL/kg) (Virbac Ltd., France), and blood samples were harvested. Finally, the aortas (from aortic arch to the bifurcation of the iliac arteries) and whole livers were collected from the rabbits after they were sacrificed for further histopathological analyses.

3. Blood Chemistry Analysis

The animals were fasted overnight before blood drawing. The blood was collected from the marginal ear veins of rabbits into BD Vacutainer EDTA Blood Collection Tubes. Plasma was separated by centrifugation at 3,000 rpm at 4° C. for 10 min. Measurements for changes in blood chemistry parameters included serum levels of low-density lipoprotein (LDL), cholesterol (Chol), triglycerides (TG), glutamate oxaloacetate transaminase (GOT), and glutamate pyruvate transaminase (GPT).

4. Aortic Fatty Streak Staining Method

The aortas were opened longitudinally to expose the intimal surface and rinsed gently with normal saline. Aortas were incubated in 2% (w/v) Sudan IV, rinsed with several concentrations (100%, 90%, 80%, 70%, and 60%) of ethanol for 1 min, and then rinsed with pure water. The photographs were acquired using a digital camera (Nikon D80, Japan) and quantified on an Alpha Imager 2200 documentation system (Alpha Innotech, USA).

5. Histopathological Examination

Conventional techniques of paraffin embedded tissues sectioning and haematoxylin-eosin (HE) staining were used in this study. Fresh specimens were cut and fixed in either alcohol or an aldehyde-based fixative. Following fixation, the tissue specimens were rinsed in $H_2O$. Then the tissue specimens were stained by Mayer's haematoxylin and 1% eosin Y and examined under a bright-field microscope.

6. Cryosectioning of Liver Tissues

The rabbit liver tissues were perfused with normal saline and fixed in 10% (v/v) formalin-neutralized solution (J.T. Baker, Inc., USA) for 24 hr. Afterward, the tissues were embedded in Tissue Tek OCT Compound (#4583; Sakura Finetek Inc., USA). Embedded tissues were cut into 10 μm thick slices and stained with Sudan IV and hematoxylin (Merck, USA). Briefly, the slices were washed with pure water for 1 min to remove the OCT compound, washed with 50% (v/v) ethanol for 30 sec, and then stained with 2% (w/v) Sudan IV for 1 hr. After further washing with 50% (v/v) ethanol and pure water for 2 min, the slices were counter-stained with hematoxylin. Photographs were acquired using a microscope equipped with a 10-fold magnification objective and quantified on an Alpha Imager 2200 documentation system (Alpha Innotech, USA). The manifestation of fatty liver progression was presented as the percentage of the area of oil droplets to the total liver tissues (cells).

7. Statistical Analysis

All values are expressed as mean±SE. Each value is the mean of at least three experiments in each drug in vitro experiments. Student's t-test is used for statistical comparison. * indicates that the values are significantly different from the control (*, $p<0.05$; **, $P<0.01$).

Example 1

Figure 2:
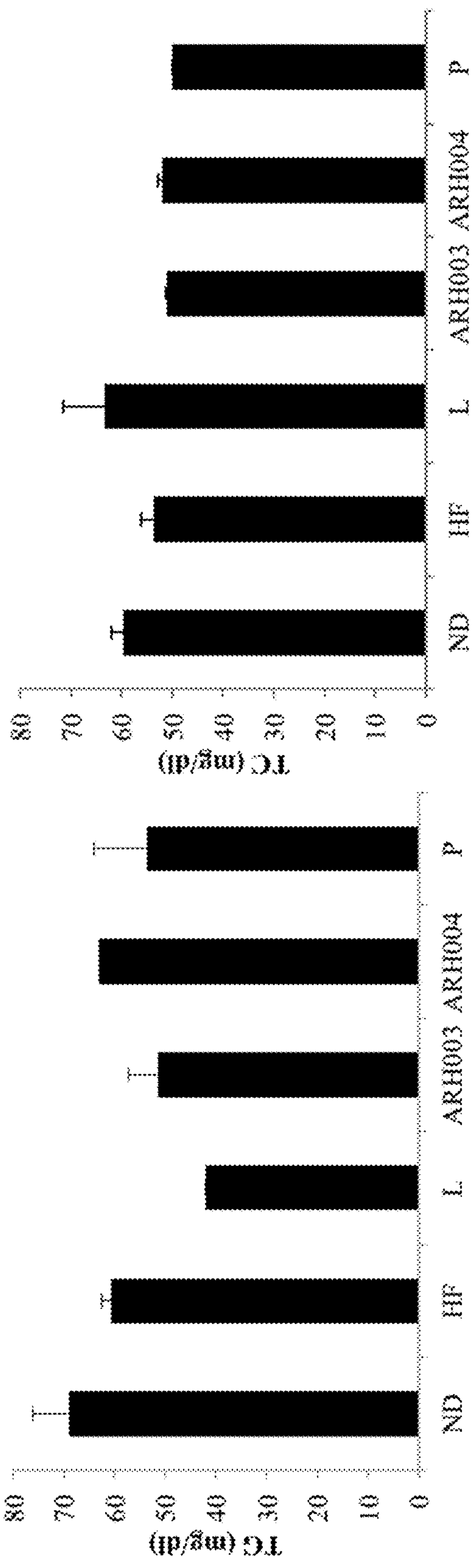
FIG. 2 shows levels of triglyceride (left panel) and total cholesterol (right panel) at week 0. ND, standard rabbit chow; HF, standard rabbit chow containing 0.5% cholesterol; L, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; P, standard rabbit chow containing both 0.5% cholesterol and 10 mg/kg Pure compound.
Figure 3:
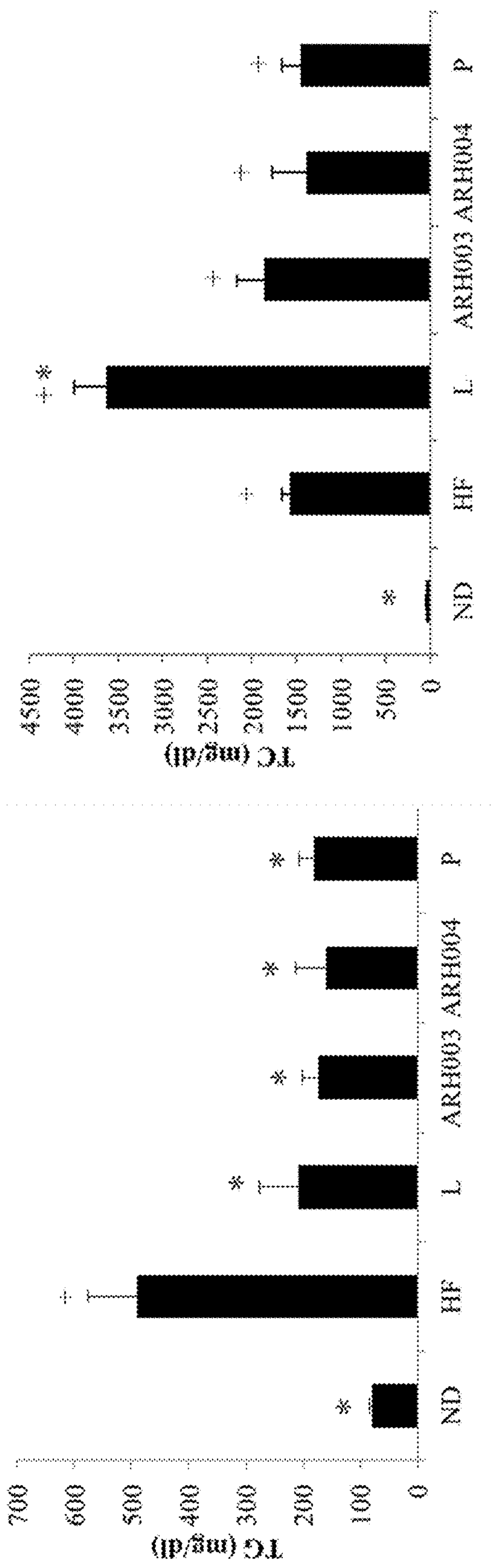
FIG. 3 shows levels of triglyceride (left panel) and total cholesterol (right panel) at week 12. ND, standard rabbit chow; HF, standard rabbit chow containing 0.5% cholesterol; L, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; P, standard rabbit chow containing both 0.5% cholesterol and 10 mg/kg Pure compound. † and * indicate a $P<0.05$ as compared with the control group and HF group, respectively.

Inhibitory Effect of *Antrodia camphorata* Fruit Body Extracts or the Derived Pure Compound on Serum Triglyceride and Total Cholesterol Levels Supplementing the high fat diet of the rabbits alone or with lovastatin, *Antrodia camphorata* fruit body extracts, or the derived pure compound did not affect the body weight gains during the intervention (FIG. 1). Furthermore, at the beginning of the treatment period, levels of triglyceride and total cholesterol among groups did not exhibit significant changes (FIG. 2). However, supplementing the high fat diet caused a significant increase in the serum triglyceride and total cholesterol levels, but the rabbits treated with *Antrodia camphorata* fruit body extracts, or the derived pure compound exhibited a significant improvement in their serum triglyceride and total cholesterol levels (FIG. 3). Of noted, the lovastatin group rabbits exhibited a higher serum total cholesterol levels compared to that of high fat diet group animals.

Example 2

Figure 4:
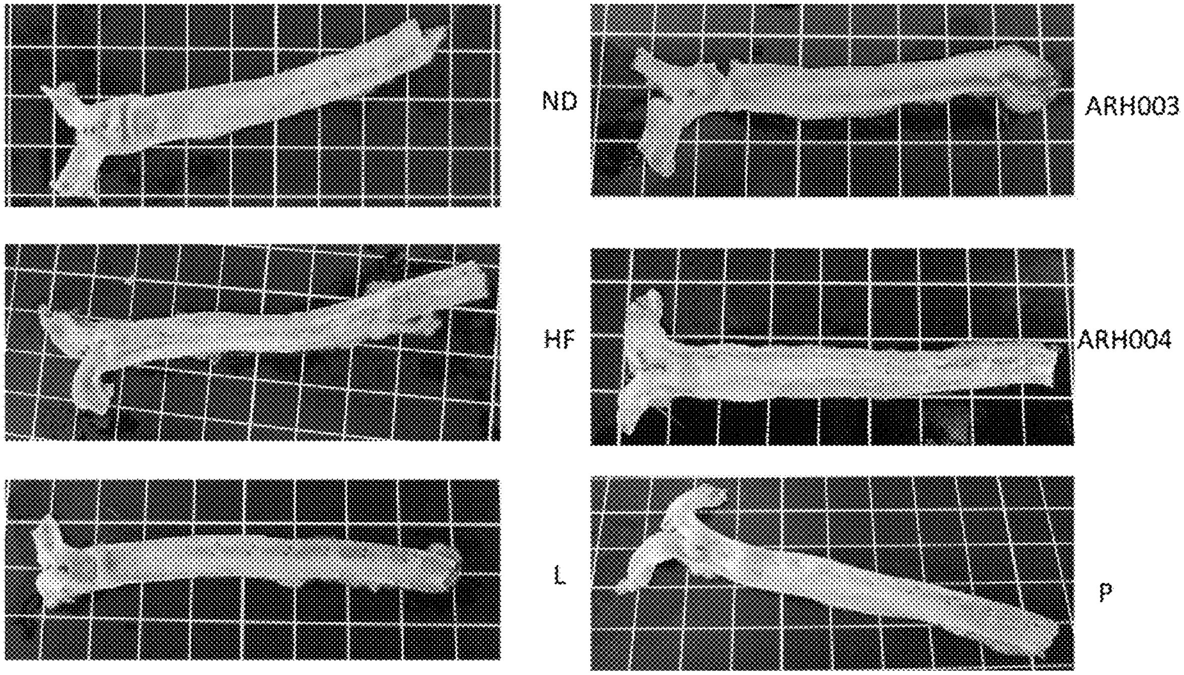
FIG. 4 shows a histopathochemical examination of aortic fatty streak lesions. ND, standard rabbit chow; HF, standard rabbit chow containing 0.5% cholesterol; L, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; P, standard rabbit chow containing both 0.5% cholesterol and 10 mg/kg Pure compound.

Inhibitory Effect of *Antrodia camphorata* Fruit Body Extracts or the Derived Pure Compound on the Formation of Fatty Steak The earliest visible lesion of atherosclerosis is the fatty streak, and with time the fatty streak evolves into a fibrous plaque, the hallmark of established atherosclerosis. Accordingly, the study on fatty streak formation revealed that *Antrodia camphorata* fruit body extracts, or the derived pure compound significantly reduced the atherosclerotic lesions as shown in FIG. 4.

Example 3

Figure 5:
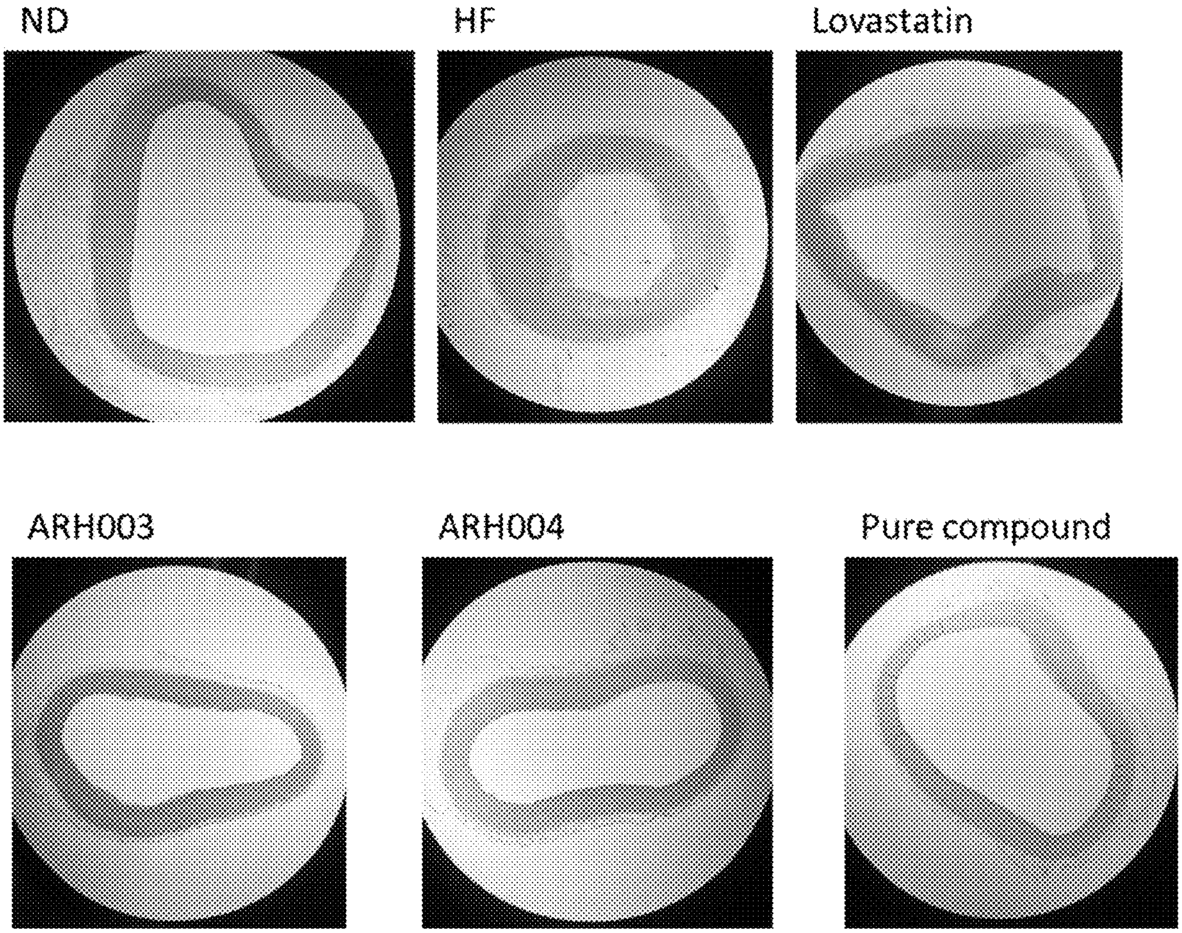
FIG. 5 shows a HE staining of coronary artery sections. ND, standard rabbit chow; HF, standard rabbit chow containing 0.5% cholesterol; Lovastatin, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; Pure compound, standard rabbit chow containing both 0.5% cholesterol and 10 mg/kg Pure compound.
Figure 6:
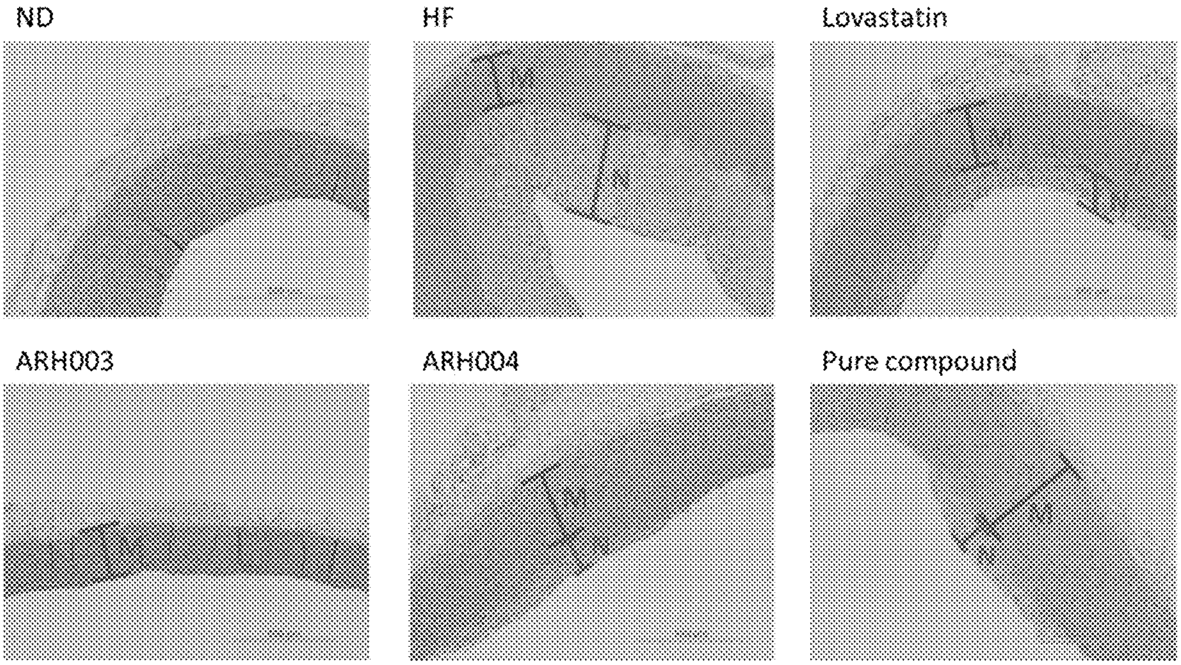
FIG. 6 shows a HE staining of coronary artery sections magnified. ND, standard rabbit chow; HF, standard rabbit chow containing 0.5% cholesterol; Lovastatin, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; Pure compound, standard rabbit chow containing both 0.5% cholesterol and 10 mg/kg Pure compound; N, neointima layer; M, media layer.
Figure 7:
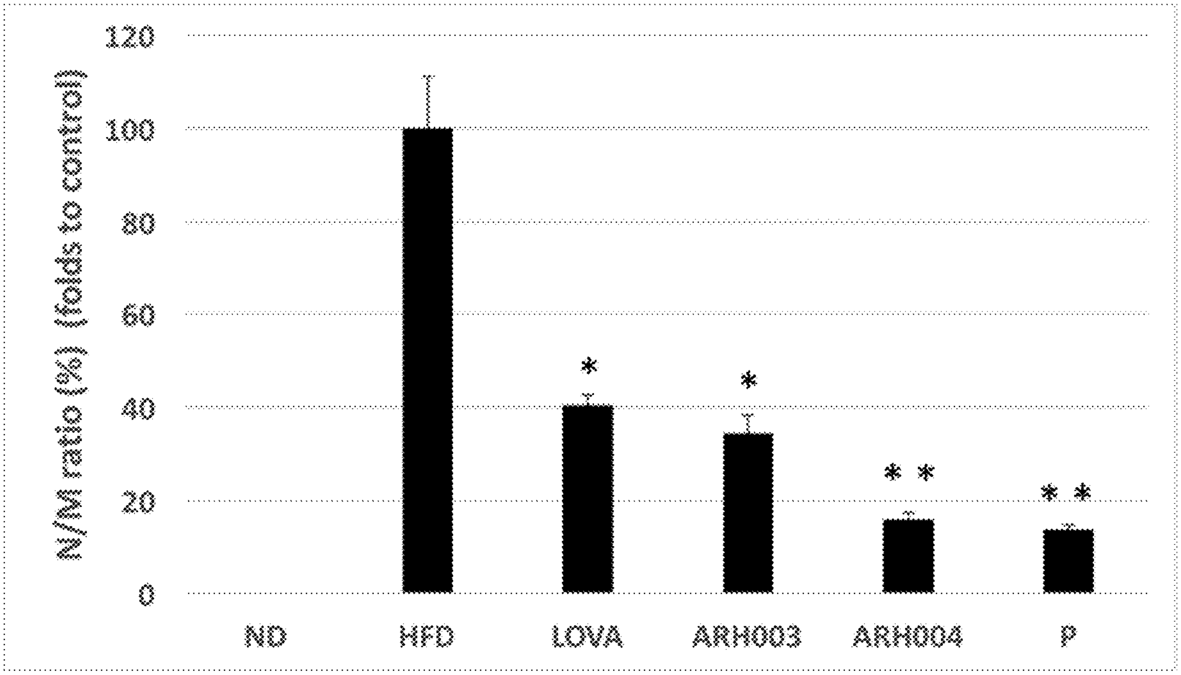
FIG. 7 shows a manifestation of vascular restenosis presented as the ratio of neointima-to-media area. ND, standard rabbit chow; HF, standard rabbit chow containing 0.5% cholesterol; Lova, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; P, standard rabbit chow containing both 0.5% cholesterol and 10 mg/kg Pure compound. * P<0.05; **, P<0.01.

Protective Effect of *Antrodia camphorata* Fruit Body Extracts or the Derived Pure Compound on the Neointimal Formation The histologic features of coronary artery of high fat diet group rabbits showed that the intimal layer becomes thicker and the diameter of the luminalis smaller due to the atherosclerotic plaques. The features of coronary artery of *Antrodia camphorata* fruit body extracts, or the derived pure compound groups rabbits showed almost normal artery without plaque (FIGS. 5 and 6). Furthermore, *Antrodia camphorata* fruit body extracts, or the derived pure compound groups rabbits displayed a >60% reduction in neointima-to-media ratio manifesting the vascular restenosis (FIG. 7).

Example 4

Figure 8:
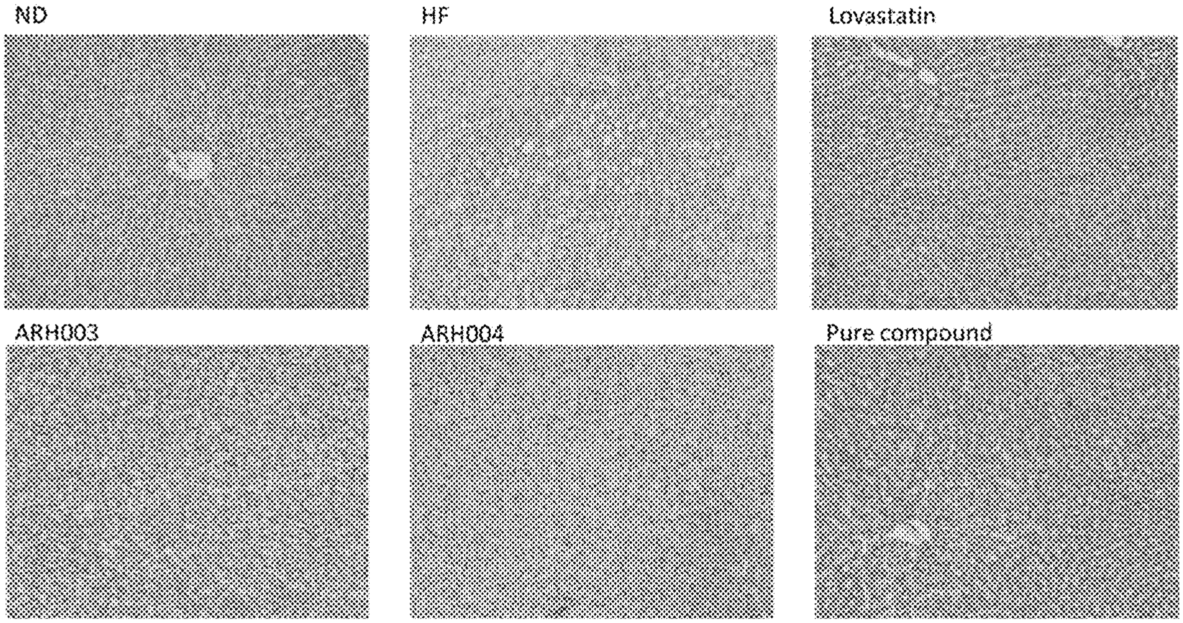
FIG. 8 shows a histopathochemical examination of liver tissues in the hypercholesterolemic rabbit model after the 12-week study. ND, standard rabbit chow; HF, standard rabbit chow containing 0.5% cholesterol; Lovastatin, standard rabbit chow containing both 0.5% cholesterol and 10 mg/kg Lovastatin; ARH003, standard rabbit chow containing both 0.5% cholesterol and 1% ARH003; ARH004, standard rabbit chow containing both 0.5% cholesterol and 1% ARH004; Pure compound, standard rabbit chow containing both 0.5% cholesterol and 10 mg/kg Pure compound.
Figure 9:
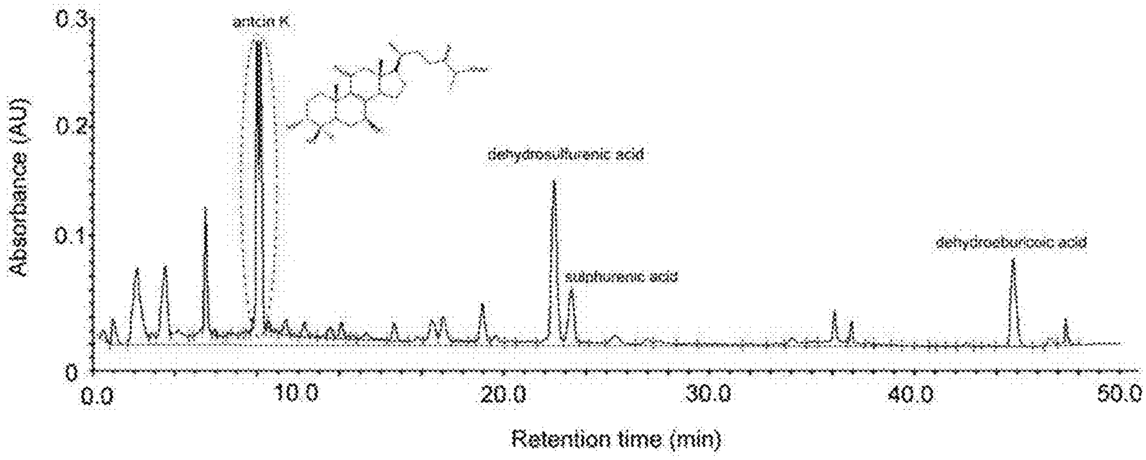
FIG. 9 provides the chromatographic fingerprint analysis by HPLC of *Antrodia camphorata* The bioactive substances present in HPLC chromatographic fingerprint were antcin K, dehydrosulfurenic acid, sulphurenic acid, versisponic acid D, and dehydroeburicoic acid. Antcin K (3a,4b,7b-trihydroxy4a-methylergosta-8,24(28)-dien-11-on-26-oic acid, 2) is an active triterpenoid from the fruiting body of *Antrodia camphorata* that was provided from ARJIL Pharmaceuticals LLC. We adopted antcin K standard products to prepare a standard solution, and analyzed and compared the standard and sample solution with the same analytical method. AU, arbitrary perfusion units; HPLC, high performance liquid chromatography.

Protective Effect of *Antrodia camphorata* Fruit Body Extracts or the Derived Pure Compound on Hepatic Lipid Accumulation As mentioned above, high fat diet-fed rabbits exhibited increased serum triglyceride and total cholesterol levels. The similar profile was further demonstrated by histopathological analysis with high-fat-diet-induced hepatic lipid accumulation, while this phenomenon was diminished by the treatment of *Antrodia camphorata* fruit body extracts or the derived pure compound (FIG. 8).

Taken together, *Antrodia camphorata* fruit body extracts or the derived pure compound disclosed herein provide protective effects on atherosclerotic plaque formation and hepatic lipid accumulation, and would be beneficial in treating atherosclerotic disease.

Example 5

Efficacy Experiment for Antcin K

Material and Method 5.1. Determination of Antcin K, an Active Triterpenoid From *Antrodia camphorata*

As shown in FIG. 1, antcin K is an active triterpenoid from the fruiting body of *Antrodia camphorata* (Yang et al., 2022). Dried *Antrodia camphorata* fruiting bodies were ground into a fine powder and extracted with 95% ethanol at ambient temperature by ARJIL Pharmaceuticals. The slurry was filtered, and the filtrate was then concentrated under low pressure to obtain a crude extract. This was followed by suspension in water and extraction with hexane and ether, which were separated using a silica gel column. The ethyl acetate and hexane were then separated by high-performance liquid chromatography (HPLC, SHIMADZU LC 20-A). Further purification yielded antcin K with >90% purity. Conditions of HPLC were summarized as follows: (a) Column: Waters/Sunfire RP18, 5 μm, 150 mm×4.6 mm ID, (b) Mobile phase: (A) 0.05% TFA aqueous solution, (B) Acetonitrile (ACN), (c) Detection: PDA ($\lambda$=220 nm), (d) Injection volume: 10 μL, (e) Analytic concentration: 0.4 mg/mL, (f) Oven temperature: 30° C., (g) Run time: 20 min.

5.2. Determination of Antioxidant Capacity of Antcin K

The antioxidant capacity of antcin K was examined by 1,1-diphenyl-2-trinitrophenylhydrazyl (DPPH) assay in this study. We formulated DPPH (D9132, Sigma-Aldrich Co., St. Louis, MO, USA) at a concentration of 1.5 mM per 1 mL and added 9 mL of methanol (322415, Sigma-Aldrich Co., St. Louis, MO, USA) to the mixed solution. The 100 μL of DPPH and 100 μL of 10, 20, and 50 μg/mL of test samples were taken, shaken, and mixed evenly, then placed at room temperature for 30 min in the dark. After that, the absorbance was measured at 517 nm using an ultraviolet/visible light spectrometer (Microplate Spectrophotometer, uQuant, Biotek Instruments, Inc., Winooski, VT, USA).

Different concentrations of test samples were prepared and compared with the standard L-Ascorbic acid (L-AA) (A5960, Sigma-Aldrich Co., St. Louis, MO, USA). Based on the reduction percentage of the absorbance value observed in the control group, the antioxidant capacity of each test sample to scavenge DPPH free radicals can be judged. After that, the test sample with the most robust ability to scavenge DPPH free radicals was selected and repeated three times. The formula is as follows: DPPH free radical scavenging rate (%)=(1−(absorption value of experimental group/absorption value of control group))×100.

5.3. Establishment of SVEC4-10 Vascular Endothelial Cell Model

Vascular endothelial cells (SVEC4-10) were purchased from the Cell Bank of Hsin-Chu Food Industry Development Institute (FIRDI, Cat no: BCRC-60220). SVEC4-10 cells were cultured in high-glucose DMEM (Dulbecco's Modified Eagle Medium) (Gibco BRL, Grand Island, NY, USA) and supplemented with 10% Fetal Bovine Serum (FBS) (HyClone, Logan, UT, USA), 1.5 g/L sodium bicarbonate, 0.11 g/L sodium pyruvate, 4 mM L-glutamine, 100 U/mL penicillin, and 100 μg/mL streptomycin (Gibco BRL, Grand Island, NY, USA).

These cells were grown in a culture medium and maintained in a humidified incubator at 37° C. and 5% CO2. Vascular endothelial cells were digested with 0.25% trypsin (Gibco BRL, Grand Island, NY, USA) for approximately 1 min until most cells detached. All cell densities were adjusted to $1\times10^5$ cells per well for each 24-well culture plate. After vascular endothelial cells were cultured for 24 h, in the hyperlipidemia group, 0.75 mM palm acid oil (CAS 57-10-3-800508; Sigma-Aldrich Co., St. Louis, MO, USA) (Oh et al., 2018) was added, and 10, 20, and 50 μg/mL of antcin K in each experiment was individually added.

5.4. Establishment of RAW264.7 Macrophage Cell Model

RAW264.7 macrophage was purchased from the Hsin-Chu Food Industry Development Institute Cell Bank (FIRDI, Cat no: BCRC-60001). The cell culture medium contains high-glucose DMEM (Gibco BRL, Grand Island, NY, USA), 10% FBS, 1.5 g/L sodium bicarbonate, 0.11 g/L sodium pyruvate, 4 mM L-glutamine, 100 U/mL penicillin, and 100 μg/mL streptomycin. These cells were maintained in a humidified incubator at 37° C. and 5% $CO_2$. After collecting the cells with a spatula, for each 24-well culture plate, all cell densities were adjusted to $1\times10^5$ cells per well for migration assays.

5.5. Cell Viability Assay

We used a 3-(4,5-Dimethylthiazol-2-yl)-2,5-diphenyltetrazolium bromide (MTT) assay to examine the cell viability of antcin K in this study. A total of $1\times10^5$ cells/mL SVEC4-10 cells were added to a 24-well plate, and 0.5 mM palm acid oil (Sigma-Aldrich Co., St. Louis, MO, USA) was partially added, and 10, 20, and 50 μg/mL of test samples were added to SVEC4-10 cells, followed by culturing within 24 h. After adding 0.5 mg/mL of MTT solution (M5655, Sigma-Aldrich Co., St. Louis, MO, USA) and culturing for 2 h, the supernatant was removed, and 100 μL/well of DMSO organic solvent was added, followed by a 5 min shaking and then absorbance measurement at 570 nm.

5.6. Enzyme-Linked Immunosorbent Assay (ELISA)

We analyzed the content of inflammatory cytokines by ELISA. The supernatant of SVEC4-10 cells with palm acid oil hyperlipidemia treatment was collected after 24 h of culture and added to a 96-well micro-well plate (Thermo Scientific Nunc®, Nunc AS, Copenhagen, Denmark). An amount of 100 μL/well of carbonate buffer containing antibodies of 32 ng/mL purified rat anti-mouse TNF-α (88-7324; Invitrogen, Carlsbad, CA, USA) or 32 ng/mL purified rat anti-mouse IL-1_(88-7013; Invitrogen, Carlsbad, CA, USA) was added to each well and kept at 4° C. overnight. After that, we washed three times with 0.05% phosphate-buffered saline with Tween 20 (PBST) buffer to remove unbound monoclonal antibodies. Then, we added 200 μL/well of blocking solution to reduce nonspecific binding. Next, we washed four times with PBST buffer, added 100 μL/well of 250_anti-cytokine secondary antibody biotin-conjugated anti-mouse TNF-α and IL-1β antibody, and reacted at room temperature for 1 h. After washing with PBST buffer five times, we added 100 μL/well of avidin-horseradish peroxidase, and the sample was reacted at room temperature for 30 min. Again, samples were washed with PBST buffer six times, reacted with 100 μL/well of tetramethylbenzidine, and kept for 20-30 min at room temperature in the dark for a reaction. The reaction was terminated with 2% H2SO4, and the absorbance at 450-570 nm was measured.

5.7. Cellular Lipid Deposition Assay

We used oil red O staining which was clearly described in a previous report (Luo et al., 2021) to examine cellular lipid deposition. RAW264.7 macrophages were fixed with 2% paraformaldehyde for 10-15 min at room temperature, washed three times with phosphate-buffered saline (PBS) and twice with ddH2O, and stained with 5% oil red O dye for 15 min at room temperature, then the supernatant was discarded. Vascular endothelial cells and RAW264.7 macrophages were infiltrated with 60% isopropanol, washed twice with ddH2O, and photographed with an optical microscope (Olympus BH2 system light microscope, Olympus Corporation, Tokyo, Japan).

5.8. Cellular Migration Assay

We used a cellular migration assay to examine the cellular migration ability of RAW 264.7 macrophages toward vascular endothelial cells with high-fat damage. The cellular migration assay has been clearly described in a previous report (Hwang et al., 2021). Transwells (Corning, New York, NY, USA) with 8.0 μm pore size were used in this experiment for cell migration assays. In total, $1\times10^5$ RAW264.7 macrophage, labeled with the red fluorescent dye of 1,1'-Dioctadecyl-6,6'-Di(4-Sulfophenyl) (SP-DiIC18(3)), was added to the upper layer of transwell after 48 h. In the lower layer of the chassis, $1\times10^5$ vascular endothelial cells were seeded in a medium with and without antcin K and palm acid oil groups, which were cultured in a humidified incubator (37° C. and 5% $CO_2$). Images were taken with a fluorescence microscope (Leica Microsystems, Wetzlar, Germany), and analysis was performed using Leica Application Suite software (LAS) V4.12 s (Leica Microsystems, Wetzlar, Germany) after 48 h of culture.

5.9. Immunofluorescence Staining

We used immunofluorescence staining to examine expressions of KLF4 and CD36. After fixing the cells on the glass slides with 2% paraformaldehyde for 10-15 min at room temperature, the tissues or cells were treated with 0.1% TritonX-100 solution for 15 min at room temperature after washing three times with 1% PBS. After that, the tissues or cells were blocked with 2% BSA for 30 min at room temperature in a humidified dark box to reduce the non-specific binding of antibodies. After washing three times with PBS, the tissues or cells were added 2% BSA to dilute the primary antibody of human anti-mouse VCAM-1 (1:200; sc-13160; Santa Cruz Biotechnology Inc., Dallas, TX, USA), rabbit antimouse KLF4 polyclone antibody (membrane protein) (1:200; GTX101508; Genetex, Irvine, CA, USA), or goat anti-mouse CD36 monoclonal antibody (1:200; sc-7309; Santa Cruz Biotechnology Inc.), and then incubated overnight in a humidified dark box at 4° C. After washing three times with PBS, the secondary antibody anti-mouse IgG-FITC (1:500) diluted with 1% BSA was added, and the cells were reacted with the cells in a humidified dark box for 1 h at room temperature. Note that this step needs to be protected from light at the beginning Nuclei were stained with 1 μg/mL diamino-2-phenilindole (DAPI) (D3286, Sigma-Aldrich Co., St. Louis, MO, USA) for 10 min at room temperature after washing three times with PBS and mounted with a fluorescent protectant-containing adhesive to reduce fluorescence decay. Fluorescent images were obtained using a Leica DM IRB inverted fluorescence microscope (Leica Microsystems, Wetzlar, Germany), and analysis was performed using Leica Application Suite software (LAS) V4.12 s (Leica Microsystems, Wetzlar, Germany). The Rhodamine fluorescence-labeled cytoskeleton was visualized at 565 nm by exciting cells at 540 nm. Cells are excited at 358 nm and emitted at 461 nm before imaging to visualize blue fluorescence-labeled nuclei.

5.10. Statistics and Data Analysis

We used the Student-Newman-Keuls (SNK) multiple comparison post hoc test to compare differences between the groups that were tested. The SNK method is a stepwise multiple comparison method used to identify sample means that are significantly different from each other. In addition, the SNK method uses a stepwise comparison method when comparing sample means. All sample means are sorted in ascending or descending order prior to mean comparison. The largest and smallest sample means are then compared within the largest range. Each group of experiments was repeated at least three times, and all experimental values were expressed as mean values+/−standard error of the mean. Differences between the groups were tested using one-way or two-way ANOVA, followed by the SNK multiple comparison post hoc tests. A p-value less than 0.05 was considered statistically significant.

5.11 Results

1. Chromatographic Fingerprint of Antcin K

Antcin K, an active triterpenoid from the fruiting body of *Antrodia camphorata* [28] was analyzed and confirmed by high-performance liquid chromatography (HPLC) detection methods. *Antrodia camphorata* was identified by external morphology and the marker compound of the plant specimen according to the Taiwan Pharmacopoeia standard. As shown in FIG. 1, the bioactive substances present in the HPLC chromatographic fingerprint of *Antrodia camphorata* were antcin K, dehydrosulfurenic acid, sulphurenic acid, versisponic acid D, and dehydroeburicoic acid. We adopted antcin K standard products to prepare a standard solution, and analyzed and compared the standard and sample solution with the same analytical method. The purity of the antcin K standard solution was greater than 90%.

2. The Free Radical Scavenging Ability of Antcin K

Figure 10:
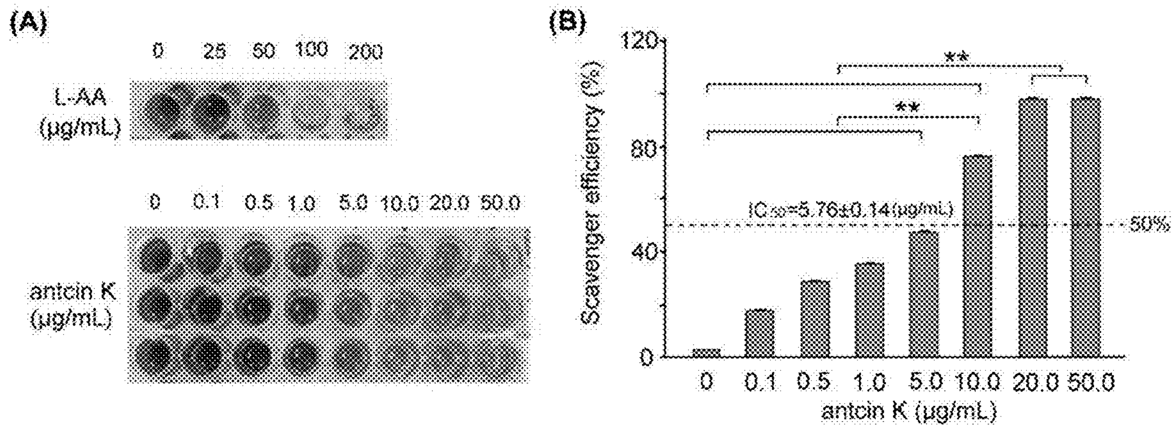
FIG. 10 shows the antioxidative capacity of antcin K.

In this study, we mainly study the alleviating effects of botanical antcin K on high-fat damage in palm acid oil-treated vascular endothelial cells and macrophages. First, we examined the effect of antcin K treatment in alleviating oxidation and clearing scavenging free radicals, as shown in FIG. 10. The DPPH free radical scavenging ability test is a simple screening test that tests whether an ingredient has antioxidant properties. DPPH (1,1-diphenyl-2-picrylhydrazyl) is a stable free radical. When it dissolves in methanol or ethanol, it will appear blue-violet. When the added component sample can react directly with the DPPH free radical, it will block DPPH in a chain reaction of free radicals. At this time, the color of the blue-purple DPPH solution will turn clear yellow, which means that the added component sample has the ability to capture DPPH free radicals, and the lighter the color, the greater the capture of DPPH free radicals. The stronger the ability, the better the antioxidant ability of this component sample. We used the DPPH assay to compare the quantified DPPH free radical scavenging activity among antcin K treatments at 0-50 μg/mL. We observed that the antcin K treatments at 20 and 50_g/mL yielded superior antioxidant activity and had good free radical scavenging efficiency (FIG. 10(A)). Compared with standard L-Ascorbic acid, the quantified free radical scavenging efficiency of antcin K is shown in FIG. 10(B). Antcin K yielded a dose-response manner in free radical scavenging efficiency as follows: 20 μg/mL and 50 μg/mL; antcin K yielded 96.82% and 98.81% of free radicals scavenging efficiency, respectively (FIG. 10(B), $p<0.001$). According to FIG. 10(B), we calculated that IC50 of free radical scavenging ability for antcin K treatments was equivalent to 5.76±0.14 μg/mL. DPPH is a stable free radical that turns blue-violet when dissolved in methanol or ethanol. The added sample can react directly with the DPPH free radical. When blocking the chain reaction of DPPH free radicals, the color of the DPPH solution will turn clear yellow. The added sample can capture DPPH free radicals in which the lighter the color, the stronger the ability to capture DPPH free radicals or the higher antioxidant capacity. As suggested in FIG. 2B, we choose 20 μg/mL antcin K to study the alleviation of high-fat damage in palm acid oil-treated vascular endothelial cells and macrophages because antcin K at 20 μg/mL should have better antioxidative capacity under high-fat damage palm acid oil treatment. In this study, the lack of antioxidant enzymes and other cellular oxidative parameters such as lipid peroxidation assays can be included in the limitations and future perspectives of the study. In the future, we hope to evaluate cellular oxidative parameters such as lipid peroxidation of botanical antcin K by lipid peroxidation (MDA) assay.

Figure 11:
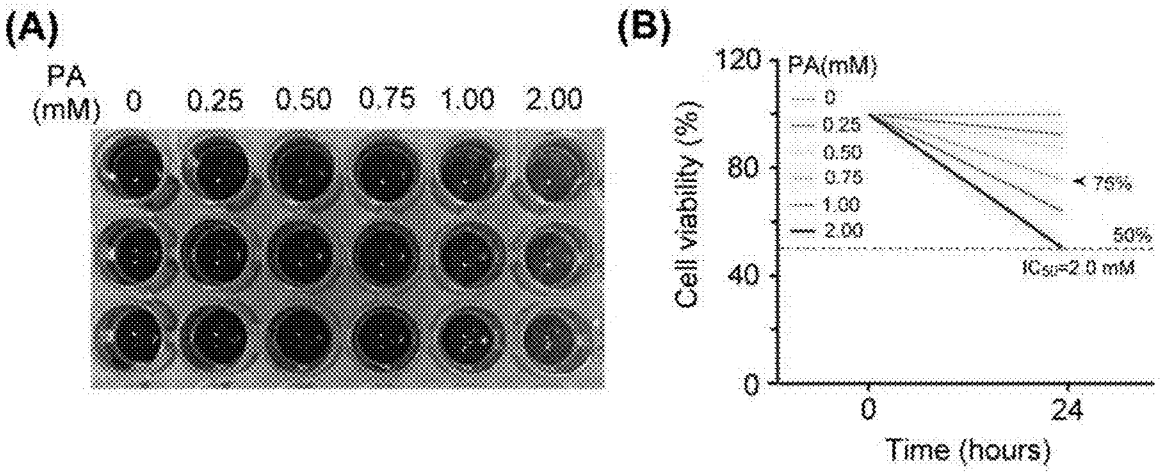
FIG. 11 shows that the palm acid oil treatment decreased the cell viability of vascular endothelial cells.

3. Antcin K Effectively Palm Acid Oil-Induced Cytotoxicity in Vascular Endothelial Cells We examined the effect of palm acid oil treatment on the cytotoxicity of vascular endothelial cells, as shown in FIG. 11. Using MTT assay, the vascular endothelial cells treated with palm acid oil (0.25-2 mM) for 24 h induced high-fat damage and reduced cell viability compared with those not treated with PA. We observed that the palm acid oil treatments at 0.25-2 mM for 24 h could induce cytotoxicity in vascular endothelial cells, as shown in FIG. 11(A). MTT assay is a staining method for detecting the mitochondria of living cells that have been clearly described in a previous report [29] (Rai et al., 2018).

This method is based on the fact that mitochondrial succinate-dehydrogenases cleave the tetrazolium ring of MTT and cause a redox reaction to form blue-purple crystals. The purple crystals were dissolved into a purple liquid by the organic solvent of dimethyl sulfoxide (DMSO), and the number of cells was converted by the shade of the generated purple color, thereby measuring the mitochondrial proliferation of cells.

From FIG. 11(B), we found that IC50 cell viability of vascular endothelial cells for palm acid oil treatment was 2.0 mM. The 75% survival rate of vascular endothelial cells induced by palm acid oil treatment was 0.75 mM. Herein, we selected palm acid oil treatment at 0.75 mM to induce high-fat damage to vascular endothelial cells and RAW264.7 macrophage cells.

Figure 12:
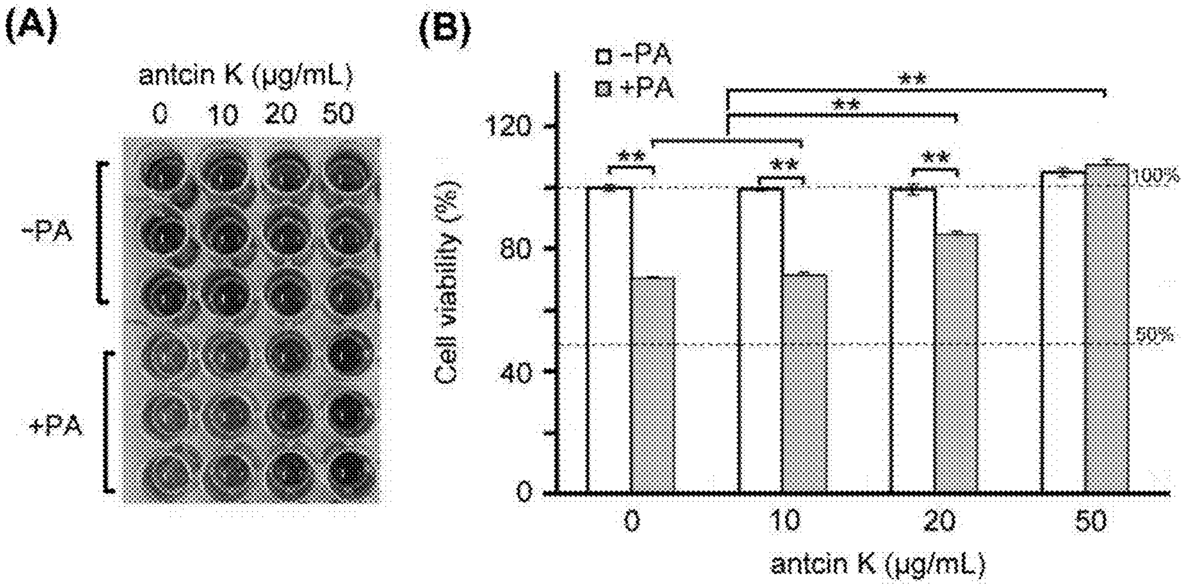
FIG. 12 shows that antcin K treatments effectively alleviated cell viability of palm oil-treated vascular endothelial cells.

Furthermore, we examined the effect of antcin K treatment in alleviating palm acid oil-induced cytotoxicity of vascular endothelial cells, as shown in FIG. 12. We found a dose-response relationship between the viability of vascular endothelial cells with palm acid oil-induced high-fat damage and concentrations of antcin K treatments (FIG. 12(B)). Our results showed that the cell viability of vascular endothelial cells decreased to 70.6% after palm acid oil treatment at 0.75 mM concentration. Compared to this, the cell viability of vascular endothelial cells increased to 71.5%, 84.6% ($p<0.05$), and 109.2% ($p<0.01$) with antcin K treatments at 10, 20, and 50_g/mL, respectively. We normalized the cell viability of vascular endothelial cells under sham treatment as 100%. Under this standard, we observed that the change of cell viability of vascular endothelial cells under 10, 20, and 50 μg/mL antcin K treatments was not very obvious without palm acid oil damage but showed a linear increase with doses of antcin K treatments with palm acid oil damage (FIG. 12(B)). Our data suggested that antcin K treatments mainly affect cell growth and reduce cytotoxicity under high-fat damage. Even higher doses of antcin K treatment can promote cell growth greater than 100%.

Figure 13:
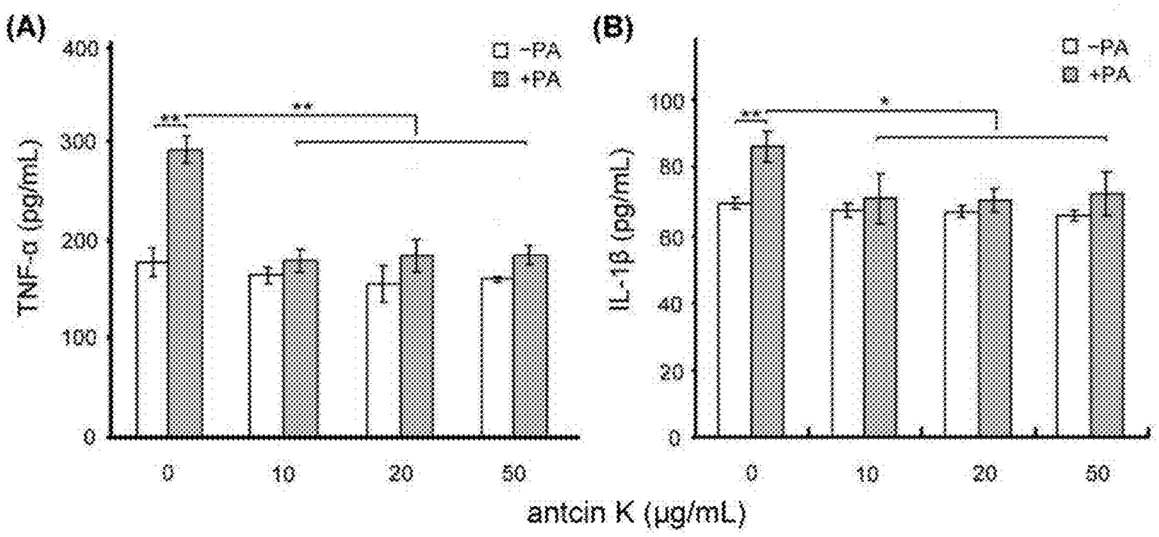
FIG. 13 shows that antcin K treatments effectively alleviated inflammation of palm oil-treated vascular endothelial cells. Comparison of the quantified expressions of the inflammatory markers TNF-α (FIG. 13(A)) and IL-1β (Figure (B)) of vascular endothelial cells with and without 0.75 mM palm acid oil (PA) treatment, and with antcin K treatments at 0, 10, 20, and 50 μg/mL (n=3 for each group; values are presented as mean±SEM, **p<0.01, * p<0.05, two-way ANOVA followed by the Student-Newman-Keuls multiple comparison post hoc test).

4. Antcin K Significantly Alleviates the Palm Acid Oil-Induced Inflammation in Vascular Endothelial Cells We examined the effect of antcin K treatment in alleviating palm acid oil-induced inflammation of vascular endothelial cells, as shown in FIG. 13. Using ELISA, the expressions of TNF-_of vascular endothelial cells were increased from 175.2 to 285.5 pg/mL after 0.75 mM palm acid oil treatment (FIG. 13(A)), and IL-1β of vascular endothelial cells were increased from 69.3 to 86.7 pg/mL after 0.75 mM palm acid oil treatment (FIG. 13(B)). After adding antcin K at 10, 20, and 50 μg/mL, the expressions of TNF-α of vascular endothelial cells were significantly decreased from 285.5 to 178.8 ($p<0.01$), 180.3 ($p<0.01$), and 181.0 pg/mL ($p<0.01$), respectively (FIG. 5A); and the expressions of IL-1β of vascular endothelial cells were decreased from 86.6 to 70.2 ($p<0.01$), 69.3 ($p<0.01$), and 71.5 pg/mL ($p<0.01$), respectively (FIG. 13(B)).

Figure 14:
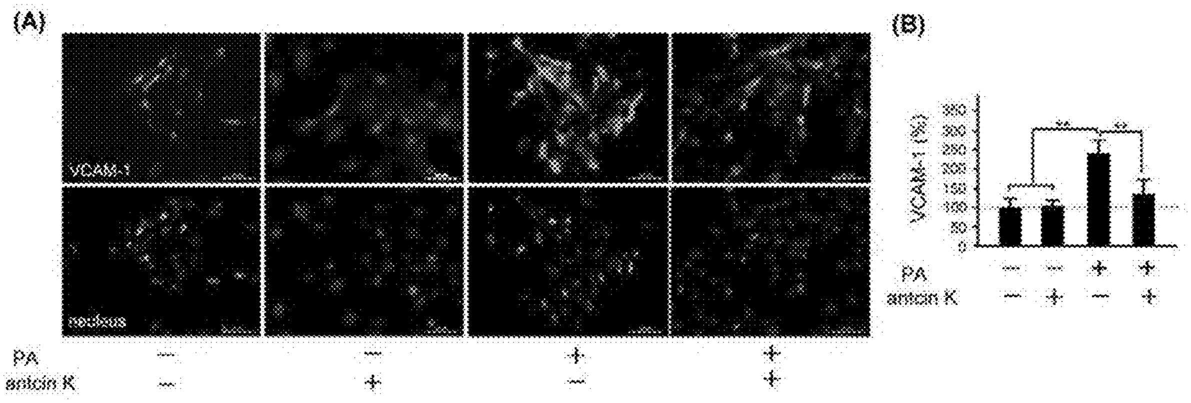
FIG. 14 shows that Antcin K treatments effectively reduced the expression of VCAM-1 in palm oil-treated vascular endothelial cells.

5. Antcin K Significantly Alleviated the Expression of VCAM-1 in Palm Acid Oil-Treated Vascular Endothelial Cells VCAM-1 adhesion molecule plays a vital role in monocyte immigration, inflammation, and atherosclerosis [9] (Nageh et al., 1997). We examined the effect of antcin K treatment in alleviating expressions of VCAM-1 in palm acid oil-treated vascular endothelial cells, as shown in FIG. 14. By immunofluorescence staining, we observed that the expression of VCAM-1 was increased in those palm acid oil-treated vascular endothelial cells without antcin K treatments. However, it was significantly decreased in those palm acid oil-treated vascular endothelial cells with 20 μg/mL antcin K treatments (FIG. 14(A)). According to our pretested data, we choose 20 μg/mL antcin K to study the alleviation of high-fat damage in palm acid oil-treated vascular endothelial cells and macrophages because antcin K at 20 μg/mL has better antioxidative capacity and cell viability under high-fat damage palm acid oil treatment. Compared with those without palm acid oil treatments, the expression of VCAM-1 was significantly increased in the vascular endothelial cells undergoing palm acid oil treatments (FIG. 14(B), $p<0.01$). It is noteworthy that 20 μg/mL antcin K treatments reduced the expression of VCAM-1 in those palm acid oil-treated vascular endothelial cells (FIG. 14(B), $p<0.01$).

Figure 15:
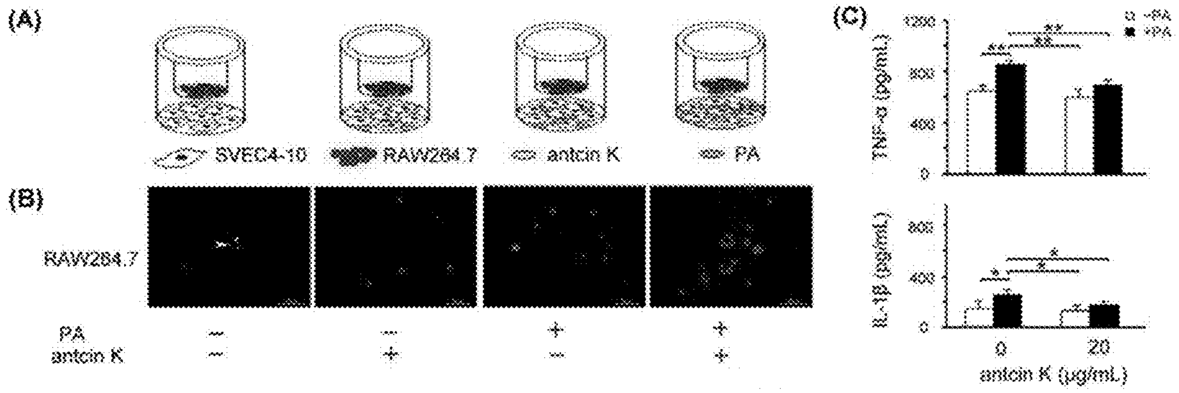
FIG. 15 shows that antcin K treatments effectively enhanced the migration ability of RAW264.7 macrophages toward palm acid oil-treated vascular endothelial cells.

6. Antcin K Treatments Effectively Enhanced the Migration Ability of RAW264.7 Macrophages toward Palm Acid Oil-Treated Vascular Endothelial Cells The effect of antcin K treatment in enhancing the migration ability of RAW264.7 macrophages toward palm acid oil-treated vascular endothelial cells is illustrated in FIG. 15. As a result, RAW264.7 macrophages were able to migrate toward palm acid oiltreated vascular endothelial cells. Furthermore, antcin K treatments enhanced RAW264.7 macrophages' migration to palm acid oil-treated vascular endothelial cells (FIG. 15(B)). Using ELISA, the expression of TNF-α of RAW264.7 macrophages significantly increased from 635.3 to 856.9 pg/mL after 0.75 mM palm acid oil treatment (FIG. 15(C), $p<0.01$); however, adding 20 μg/mL antcin K could reduce the expression of TNF-α from 856.9 to 690.7 (FIG. 15(C), $p<0.01$) Similarly, the expression of IL-1β of RAW264.7 macrophage cells also increased from 152.3 to 272.3 pg/mL under 0.75 mM palm acid oil (FIG. 15(C), $p<0.05$) and decreased from 272.3 to 189.2 after adding 20 μg/mL antcin K (FIG. 15(C), $p<0.05$).

Figure 16:
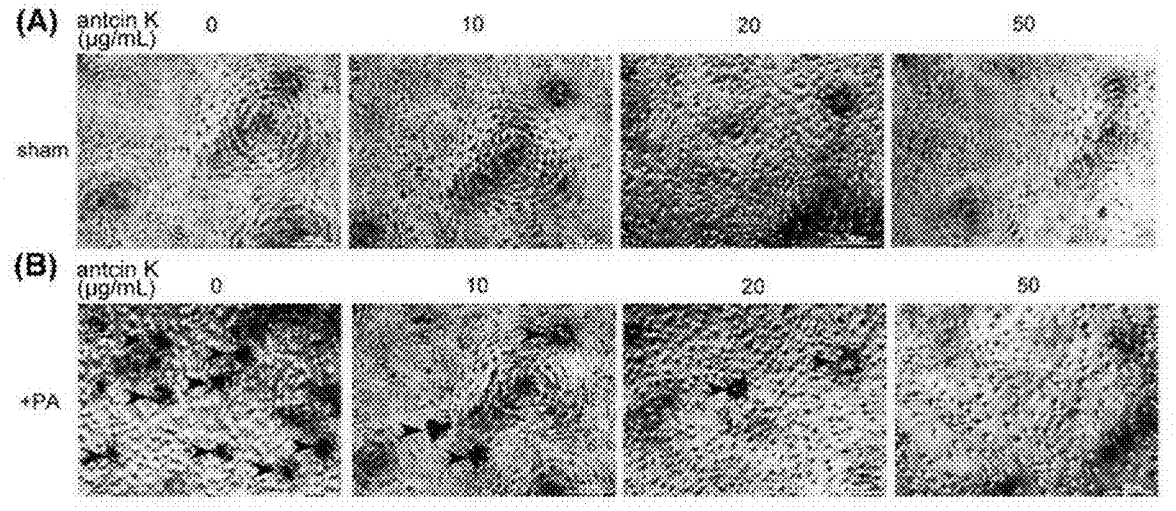
FIG. 16 shows that antcin K treatments effectively decreased the lipid deposition in palm acid oil-treated vascular endothelial cells. Vascular endothelial cells with sham (FIG. 16(A)) and palm acid oil (PA) treatment (FIG. 16(B)). Cellular lipid depositions were shown by oil red O staining (indicated by the arrow).

7. Antcin K Effectively Alleviated Lipid Deposition of Palm Acid Oil-Treated Vascular Endothelial Cells We examined the effect of antcin K treatment in alleviating lipid deposition of palm acid oil-treated vascular endothelial cells using oil red O staining (FIG. 16). Although lipid deposition was almost invisible in those vascular endothelial cells that did not receive palm acid oil (FIG. 16(A)), it was obviously seen in palm acid oil-treated vascular endothelial cells (FIG. 16(B)). Furthermore, we applied different concentrations of antcin K in the palm acid oil-treated vascular endothelial cells and found that lipid deposition decreased with concentrations of antcin K treatments (FIG. 16(B)).

Figure 17:
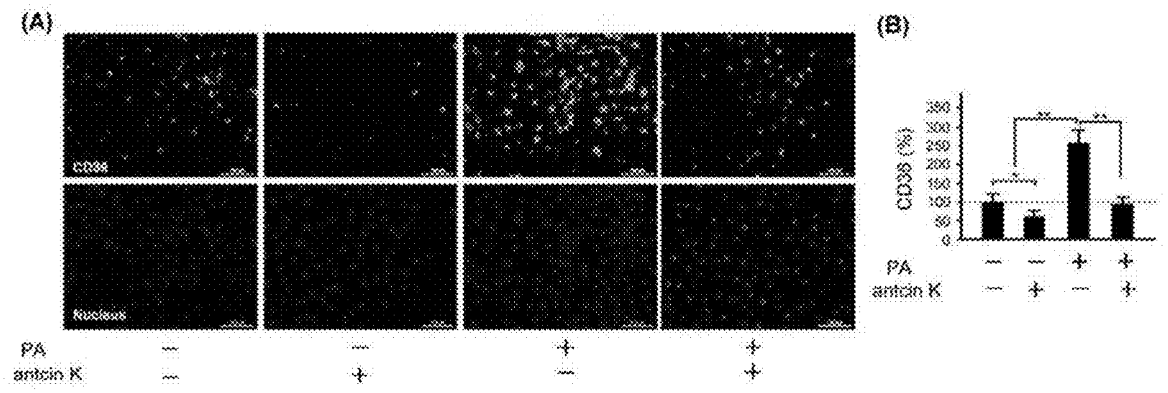
FIG. 17 shows that antcin K treatments effectively reduced the expression of CD36 in palm oil-treated vascular endothelial cells.

8. Antcin K Significantly Decreased the Expression of CD36 in Palm Oil-Treated Vascular Endothelial Cells Scavenger receptors expressed in vascular endothelial cells and macrophages, especially CD36, are the primary marker that transforms lipid-deposited macrophages into foam cells. We examined the effect of antcin K treatment concerning the expression of CD36 in palm acid oil-treated vascular endothelial cells, as shown in FIG. 17. By immunofluorescence staining, we observed that the expression of CD36 was obviously increased in those palm oil-treated vascular endothelial cells without antcin K treatments but was decreased in those palm oil-treated vascular endothelial cells with 20 μg/mL antcin K treatments (FIG. 17(A)). Compared with those vascular endothelial cells without palm acid oil treatments, the expression of CD36 was significantly increased in those vascular endothelial cells with palm acid oil treatments (FIG. 17(B), $p<0.01$).

Figure 18:
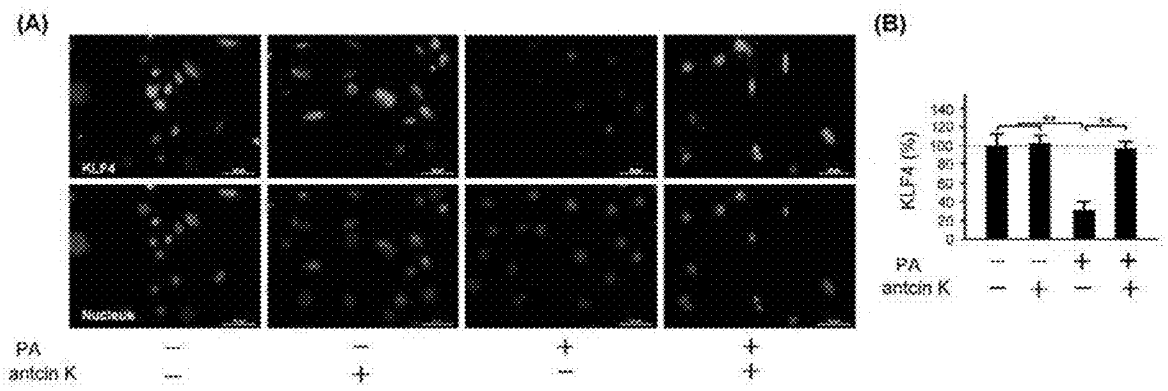
FIG. 18 shows that antcin K treatments effectively enhanced the expression of KLF4 in palm oil-treated vascular endothelial cells.

9. Antcin K Significantly Enhanced the Expression of KLF4 in Palm Oil-Treated Vascular Endothelial Cells KLF4 plays a crucial role in inhibiting LDL transport and foam cell formation in vascular endothelial cells and macrophages. We examined the effect of antcin K treatment in enhancing the expression of KLF4 in palm acid oil-treated vascular endothelial cells in FIG. 18. Immunofluorescence staining showed that KLF4 expression was reduced in palm acid oil-treated vascular endothelial cells without the existence of antcin K treatment; but it was enhanced under 20 μg/mL antcin K treatment (FIG. 18(A)). With palm acid oil treatment, vascular endothelial cells were significantly less likely to express KLF4 than those without palm acid oil treatment (FIG. 18(B), $p<0.01$). In addition, 20 μg/mL antcin K significantly increased the expression of KLF4 in palm acid oil-treated vascular endothelial cells (FIG. 18(B), $p<0.01$).

Figure 19:
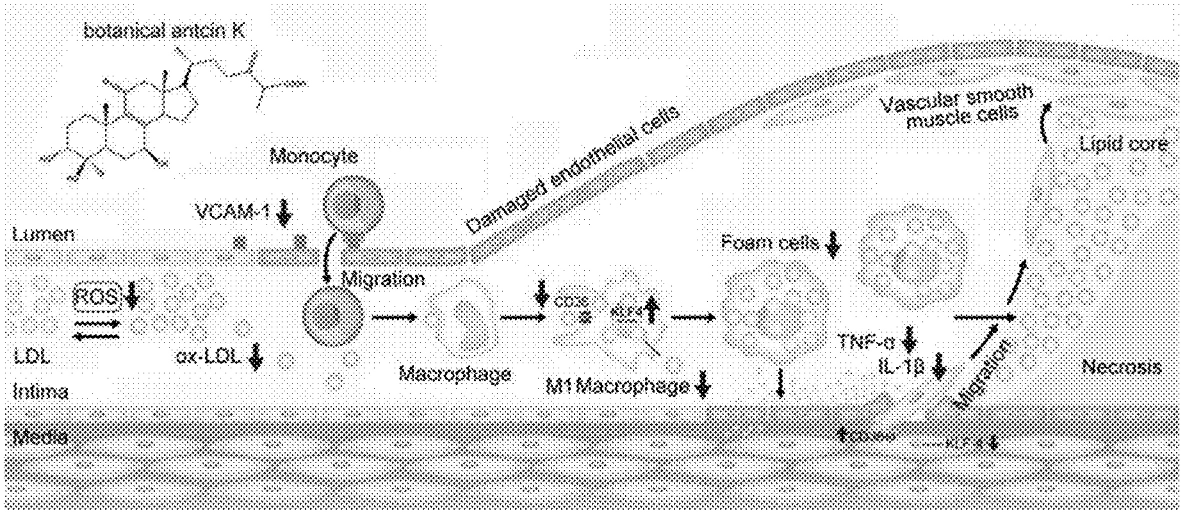
FIG. 19 provides a diagram showing possible therapeutic mechanisms of antcin K in alleviating the high-fat damage of vascular endothelial cells and macrophages in blood vessels.

Given the above, it can be concluded that antcin K alleviates the high-fat damage of vascular endothelial cells and macrophages in blood vessels, the possible therapeutic mechanisms is given in FIG. 19. That is, antcin K treatment can (1) decrease the expression of VCAM-1 that alleviates circulating monocytes adhering to endothelial cells and migrating into subendothelial space; (2) reduce ROS generation and oxidative stress that alleviate the oxidative modification of lipoproteins and phospholipids; (3) enhance the expression of KLF4 in macrophages and endothelial cells that decrease lipid deposition and prevent macrophages converting into foam cells; (4) decrease the content of TNF-α and IL-1β; and (5) decrease the expression of CD36 that slows transformation of macrophages and endothelial cells to foam cells.

The above description merely relates to preferred embodiments in the present invention, and it should be pointed out that, for a person of ordinary skill in the art, some improvements and modifications can also be made under the premise of not departing from the principle of the present invention, and these improvements and modifications should also be considered to be within the scope of protection of the present invention.

What is claimed is:

1. A method for alleviating circulating monocytes adhering to endothelial cells and migrating into subendothelial space, and alleviating oxidative modification of lipoproteins and phospholipids; decreasing lipid deposition and preventing macrophages converting into foam cells; and slowing transformation of macrophages and endothelial cells to foam cells in a subject suffering with atherosclerosis, which comprises administering to said subject an effective amount of a composition or pharmaceutical composition containing antcin K having the structure below:

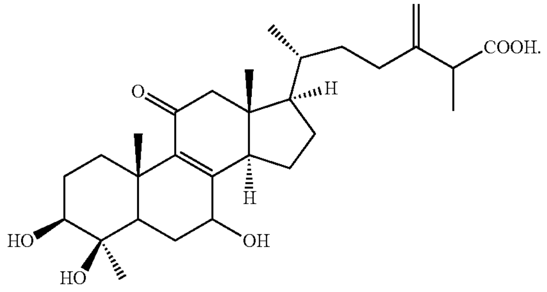 [SMILES: C=C(CC[C@@H](C)[C@H]1CC[C@H]2C3=C(C(=O)C[C@]12C)[C@@]1(C)CC[C@H](O)[C@](C)(O)C1CC3O)C(C)C(=O)O]

2. The method of claim 1, wherein the antcin K decreases the expression of VCAM-1 that alleviates circulating monocytes adhering to endothelial cells and migrating into subendothelial space.

3. The method of claim 1, wherein the antcin K reduces ROS generation and oxidative stress that alleviate the oxidative modification of lipoproteins and phospholipids.

4. The method of claim 1, wherein the antcin K enhances the expression of KLF4 in macrophages and endothelial cells that decrease lipid deposition and prevent macrophages converting into foam cells.

5. The method of claim 1, wherein the antcin K decreases the content of TNF-α and IL-1β.

6. The method of claim 1, wherein the antcin K decreases the expression of CD36 that slows transformation of macrophages and endothelial cells to foam cells.

* * * * *